US006242584B1

(12) United States Patent
Kook et al.

(10) Patent No.: US 6,242,584 B1
(45) Date of Patent: Jun. 5, 2001

(54) METHOD FOR IDENTIFYING MYCOBACTERIAL SPECIES BY COMPARATIVE SEQUENCE ANALYSIS OF RPOB GENE

(75) Inventors: Yoon-Hoh Kook; Bum-Joon Kim, both of Seoul (KR)

(73) Assignee: Bioneer Corporation, Chooncheongbuk-Do (KR)

( * ) Notice: Subject to any disclaimer, the term of this patent is extended or adjusted under 35 U.S.C. 154(b) by 0 days.

(21) Appl. No.: 09/147,935

(22) PCT Filed: Jul. 28, 1998

(86) PCT No.: PCT/KR98/00228

§ 371 Date: Mar. 19, 1999

§ 102(e) Date: Mar. 19, 1999

(87) PCT Pub. No.: WO99/05316

PCT Pub. Date: Feb. 4, 1999

(30) Foreign Application Priority Data

Jul. 28, 1997 (KR) .................................... 97/35501

(51) Int. Cl.$^7$ ............................ C07H 21/02; C07H 21/04

(52) U.S. Cl. ................................ 536/23.1; 536/24; 536/3

(58) Field of Search .......................... 435/6, 91.1, 91.2, 435/863; 536/24.33, 24.32; 935/8

(56) References Cited

U.S. PATENT DOCUMENTS

5,643,723   7/1997   Persing et al. ................... 435/6

FOREIGN PATENT DOCUMENTS

| 0 584 023 A1 | 2/1994 | (EP) . |
| WO 95/33074 A1 | 12/1995 | (WO) . |
| WO 97/16564 A1 | 5/1997 | (WO) . |

OTHER PUBLICATIONS

Reference A: STN Commerical Database, Genembl, Accession No. L27989, Sep. 1994.*
Miller et al., "The rpoB Gene of *Mycobacterium tuberculosis*," Antimicrobial Agents and Chemotherapy, 1994, vol. 38, No. 4, pp. 805–811.*
A. Devallois et al., Molecular Characterization of *Mycobacterium avium* Complex Isolates Giving Discordant Results in AccuProbe Tests by PCR–Restriction Enzyme Analysis, 16s rRNA Gene Sequencing, and DT 1–DT6 PCR, J. Clin. Microbiol., 35(11):2767–2772 (1997).
Amalio Telenti et al., Detection of Rifampicin–Resistance Mutations in *Mycobacterium Tuberculosis*, The Lancet 341:647–650 (1993).
Anne Devallois et al., Rapid Identification of Mycobacteria to Species Level by PCR–Restriction Fragment Length Polymorphism Analysis of the hsp65 Gene and Proposition of an Algorithm to Differentiate 34 Mycobacterical Species, J. Clin. Microbiol., 35(11):2969–2973.
Bum–Joon Kim et al., Mutations in the rpoB Gene of *Mycobacterium tuberculosis* that Interfere with PCR–Single–Strand Conformation Polymorphism Analysis for Rifampin Susceptibility Testing, J. Clin. Microbiol., 35(2):492–494.
Burkhard Springer et al., Two–Laboratory Collaborative Study on Identification of Mycobacteria: Molecular Versus Phenotypic Methods, J. Clin. Microbiol., 34(2):296–303 (1996).
George E. Fox et al., How Close is Close: 16s rRNA Sequence Identity May Not Be Sufficient To Guarantee Species Identity, Int. J. Syst. Bacteriol., 42(1):166–170 (1992).
Lawrence G. Wayne and Hilda A. Sramek, Agents of Newly Recognized or Infrequently Encountered Mycobacterial Diseases, Clin. Microbiol. Rev., 5(1):1–25 (1992).
Lincoln P. Miller et al., The rpoB Gene of *Mycobacterium tuberculosis*, Antimicrob. Agents Chemother., 38(4):805–811 (1994).
Michael Alekshun et al., Molecular Cloning and Characterization of *Borrelia burgdorferi* rpoB, Gene 186:227–235 (1997).
M.A. Picardeau et al., Genotypic Characterization of Five Subspecies of *Mycobacterium Kansasii*, J. Clin. Microbiol., 35(1):25–32 (1997).
Rogall T. et al., Towards a Phylogeny and Definition of Species at the Molecular Level with in the Genus Mycobacterium, Int. J. Syst. Bacteriol., 40(4):323–330 (1990).

(List continued on next page.)

Primary Examiner—John S. Brusca
Assistant Examiner—Young Kim
(74) Attorney, Agent, or Firm—Darby & Darby

(57) ABSTRACT

The present invention relates to a method for detecting and identifying mycobacterial species which comprises steps of amplifying 342 bp of rpoB gene fragments from clinically isolated mycobacterial using mycobacterial rpoB-specific PCR primers; sequencing 306 bp regions of the amplified 342 bp of rpoB gene fragments except the primer regions; and, inferring a phylogenetic tree with reference species. In accordance with the present invention, it was found that rpoB sequences from 44 mycobacterial species provide a basis for systematic phylogenetic relationship which can be used to identify clinically isolated mycobacteria that are pathogenic or potentially so. Accordingly, the amplification of rpoB DNA followed by automated sequencing and the analysis of phylogenetic relationships with the reference species can be used efficiently to detect and identify clinical isolates of mycobacteria which have not been identified by the conventional methods. In particular, this approach is useful for slowly growing, fastidious or uncultivable mycobacteria. Furthermore, in the case of *M. tuberculosis*, rifampin susceptibility can be simultaneously determined. Thus, the PCR-mediated comparative sequence analysis of rpoB DNA of the invention can be regarded as a reliable and rapid method for the diagnosis of mycobacterial infection.

49 Claims, 11 Drawing Sheets

OTHER PUBLICATIONS

Seth V. Hetherington et al., Sequence and Analysis of the rpoB Gene of *Mycobacterium smegmatis*, Antimicrob. Agents Chemother., 39(9):2164–2166 (1995).

Thomas R. Gingeras et al., Simultaneous Genotyping and Species Identification Using Hybridization Pattern Recognition Analysis of Generic Mycobacterium DNA Arrays, Genome Res., 8:435:448 (1998).

Till Rogall et al., Differentiation of Mycobacterium Species by Direct Sequencing of Amplified DNA, J. Gen. Microbiol., 136:1915–1920 (1990).

* cited by examiner

FIG. 1A

```
                            10         20         30
M. abscessus             TGCGTACCGT CGGCGAGCTG ATTCAGAACC
M. africanum             TGCGTACGGT CGGCGAGCTG ATCCAAAACC
M. asiaticum             TGCGCACCGT GGGCGAGTTG ATCCAGAACC
M. aurum                 TGCGTACCGT CGGCGAGCTG ATCCAGAACC
M. avium                 TGCGCACCGT CGGTGAGCTG ATCCAGAACC
M. bovis                 TGCGTACCGT CGGCGAGCTG ATCCAAAACC
M. bovis. BCG            TGCGTACGGT CGGCGAGCTG ATCCAAAACC
M. celatum Type 1        TTCGTACCGT CGGTGAGCTG ATCCAGAACC
M. celatum Type 2        TTCGTACCGT CGGCGAGCTG ATCCAGAACC
M. chelonae              TGCGTACCGT CGGCGAGCTG ATCCAGAACC
M. chitae                TGCGCACCGT GGGTGAGCTG ATCCAGAACC
M. fallax                TGCGCACCGT GGGCGAGCTG ATCCAGAACC
M. flavescense           TGCGCACCGT CGGCGAGCTG ATCCAGAACC
M. fortuitum             TGCGCACCGT GGGCGAGCTG ATCCAGAACC
M. fortuitum 49403       TGCGCACCGT GGGCGAGCTG ATCCAGAACC
M. gastri                TGCGCACGGT GGGCGAGCTG ATCCAGAACC
M. genavense             TGCGCACGGT GGGCGATCTG ATCCAGAACC
M. gordonae              TGCGCACCGT GGGCGAGCTG ATCCAGAACC
M. haemophilum           TGCGCACGGT CGGCGAATTG ATCCAGAACC
M. interjectum           TGCGTACCGT CGGCGAGCTG ATCCAGAACC
M. intermedium           TGCGCACCGT CGGTGAGCTG ATCCAGAACC
M. intracellulare        TGCGCACCGT GGGTGAGCTG ATCCAGAACC
M. kansasii              TGCGTACCGT CGGCGAGCTG ATCCAGAACC
M. leprae (Thai 53)      TGCGCACGGT CGGCGAATTG ATCCAGAACC
M. malmoense             TGCGCACGGT CGGGGAGCTG ATCCAGAACC
M. marinum               TGCGCACGGT GGGTGAGCTG ATCCAGAACC
M. neoaurum              TGCGCACCGT GGGTGAGCTG ATCCAGAATC
M. nonchromogenicum      TGCGCACCGT GGGTGAGCTG ATCCAGAACC
M. paratuberculosis      TGCGCACCGT CGGTGAGCTG ATCCAGAACC
M. peregrinum            TGCGCACCGT CGGTGAGCTG ATCCAGAACC
M. phlei                 TGCGCACCGT CGGCGAGCTG ATCCAGAACC
M. scrofulaceum          TGCGCACCGT CGGGGAGCTG ATCCAGAACC
M. senegalense           TGCGCACCGT GGGTGAGCTG ATCCAGAACC
M. shimoidei             TGCGCACGGT GGGTGAGCTG ATCCAGAACC
M. simiae                TGCGCACGGT GGGCGAACTG ATCCAAAACC
M. smegmatis             TGCGCACCGT CGGTGAGCTG ATCCAGAACC
M. szulgai               TGCGCACCGT GGGCGAGTTG ATTCAGAACC
M. terrae                TGCGCACGGT GGGTGAGCTG ATCCAGAACC
M. thermoresistable      TGCGCACCGT CGGCGAGCTG ATCCAGAACC
M. triviale              TGCGCACCGT CGGGGAGTTG ATCCAGAACC
M. tuberculosis          TGCGTACGGT CGGCGAGCTG ATCCAAAACC
M. ulcerans              TGCGCACGGT GGGTGAGCTG ATCCAGAACC
M. vaccae                TGCGCACGGT CGGTGAGCTG ATCCAGAACC
M. xenopi                TGCGCACGGT CGGCGAGCTG ATCCAAAACC C. diphtheriae           TGCGTACCGT CGGCGAGCTG ATCCAAAACC
N. nova                  TCCGCACGGT CGGCGAGTTG ATCCAGAACC
R. equi                  TGCGCACGGT GGGCGAGCTG ATCCAGAACC
```

FIG. 1B

```
           40         50         60         70
    AGATCCGGGT CGGCCTGTCC CGTATGGAGC GCGTCGTGCG
    AGATCCGGGT CGGCATGTCG CGGATGGAGC GGGTGGTCCG
    AGATCCGGGT CGGCATGTCC CGGATGGAGC GCGTCGTCCG
    AGATCCGCGT CGGCCTCTCG CGTATGGAGC GTGTCGTGCG
    AGATCCGGGT CGGCATGTCC CGGATGGAGC GCGTCGTCCG
    AGATCCGGGT CGGCATGTCG CGGATGGAGC GGGTGGTCCG
    AGATCCGGGT CGGCATGTCG CGGATGGAGC GGGTGGTCCG
    AGATCCGAGT CGGCATGTCC CGCATGGAGC GGGTGGTCCG
    AGATCCGGGT CGGTATGTCG AGGATGGAGC GGGTGGTCCG
    AGATCCGGGT CGGCCTGTCG CGTATGGAGC GCGTCGTGCG
    AGATCCGGGT CGGCCTGTCC CGCATGGAGC GCGTCGTGCG
    AGATCCGGGT CGGCCTGTCC CGGATGGAGC GCGTCGTCCG
    AGATCCGGGT CGGCCTGTCG CGGATGGAGC GCGTCGTCCG
    AGATCCGCGT CGGCCTGTCC CGCATGGAGC GCGTCGTGCG
    AGATCCGGGT CGGCCTGTCC CGCATGGAGC GCGTCGTGCG
    AGATCCGGGT CGGCATGTCC AGGATGGAGC GCGTCGTCCG
    AGATCCGGGT CGGCATGTCG CGGATGGAGC GGGTGGTCCG
    AGATCCGGGT CGGCATGTCC CGGATGGAGC GCGTCGTGCG
    AGATCCGGGT CGGCATGTCG CGGATGGAGC GGGTGGTCCG
    AGATCCGGGT CGGCATGTCC CGCATGGAGC GCGTTGTCCG
    AGATCCGGGT CGGCATGTCC AGGATGGAGC GCGTCGTCCG
    AGATCCGGGT CGGCATGTCG CGGATGGAGC GCGTCGTCCG
    AGATCCGGGT CGGCATGTCG AGGATGGAGC GGGTGGTCCG
    AGATCCGGGT CGGTATGTCG CGGATGGAGC GGGTGGTCCG
    AGATCCGCGT CGGCATGTCG CGGATGGAGC GCGTCGTCCG
    AGATCCGGGT CGGCATGTCG CGGATGGAGC GGGTGGTCCG
    AGATCCGGGT CGGCCTGTCG CGCATGGAGC GCGTCGTGCG
    AGATCCGGGT CGGGCTGTCC CGGATGGAGC GCGTGGTCCG
    AGATCCGGGT CGGCATGTCC CGGATGGAGC GCGTCGTCCG
    AGATCCGGGT CGGCCTGTCG CGTATGGAGC GTGTCGTGCG
    AGATCCGGGT CGGCCTGTCG CGTATGGAGC GCGTCGTGCG
    AGATCCGGGT CGGCATGTCC CGCATGGAGC GGGTCGTCCG
    AGATCCGGGT CGGCCTGTCC CGCATGGAGC GCGTCGTGCG
    AGATCCGGGT CGGCATGTCG CGGATGGAGC GGGTGGTCCG
    AGATCCGCGT CGGCATGTCG CGTATGGAGC GTGTCGTCCG
    AGATCCGCGT GGGCCTGTCC CGCATGGAGC GTGTCGTGCG
    AGATCCGGGT CGGCATGTCC CGGATGGAGC GCGTCGTGCG
    AGATCCGGGT CGGGTTGTCC CGGATGGAGC GTGTGGTCCG
    AGATCCGGGT CGGCCTGTCC CGCATGGAGC GCGTCGTGCG
    AGATCCGGGT CGGGCTGTCC CGGATGGAGC GGGTGGTCCG
    AGATCCGGGT CGGCATGTCG CGGATGGAGC GGGTGGTCCG
    AGATCCGGGT CGGCATGTCG CGGATGGAGC GGGTGGTCCG
    AGATCCGCGT CGGCCTCTCG CGTATGGAGC GTGTCGTCCG
    AGATCCGGGT CGGCATGTCG AGGATGGAGC GGGTGGTCCG

AGGTTCGTGT GGGTCTCTCC CGCATGGAGC GCGTTGTTCG
    AGATCCGCGT CGGCCTCTCG CGGATGGAGC GGGTGGTCCG
    AGATCCGCGT GGGCCTGTCC CGCATGGAGC CCGTCGTCCG
```

FIG. 1C

```
          80         90         100        110        120
TGAGCGCATG ACCACGCAGG ACGTCGAGGC GATCACCCCG CAGACCCTGA
GGAGCGGATG ACCACCCAGG ACGTGGAGGC GATCACACCG CAGACGTTGA
CGAGCGGATG ACCACTCAGG ACGTCGAGGC GATCACGCCG CAGACCCTGA
TGAGCGCATG ACCACCCAGG ACGTCGAGGC GATCACGCCG CAGACCCTGA
CGAGCGGATG ACCACCCAGG ACGTCGACGC CATCACGCCG CAGACCCTGA
GGAGCGGATG ACCACCCAGG ACGTGGAGGC GATCACACCG CAGACGTTGA
GGAGCGGATG ACCACCCAGG ACGTGGAGGC GATCACACCG CAGACGTTGA
CGAGCGGATG ACCACTCAGG ACGTCGAGGC GATCACGCCG CAGACCCTGA
CGAGCGGATG ACCACCCAGG ACGTCGAGGC GATCACGCCG CAGACCCTGA
TGAGCGCATG ACCACTCAGG ACGTCGAGGC GATCACCCCG CAGACCCTGA
CGAGCGGATG ACCACCCAGG ACGTCGAGGC CATCACGCCG CAGACCCTGA
CGAGCGGATG ACCACCCAGG ACGTCGAGGC GATCACCCCG CAGACCCTGA
TGAGCGGATG ACCACCCAGG ACGTCGAGGC GATCACGCCG CAGACCCTGA
TGAGCGCATG ACCACCCAGG ACGTCGAGGC GATCACCCCG CAGACCCTGA
TGAGCGCATG ACCACCCAGG ACGTCGAGGC GATCACCCCG CAGACCCTGA
GGAGCGGATG ACCACTCAGG ACGTCGAGGC CATCACGCCG CAGACGCTGA
TGAGCGGATG ACCACTCAGG ACGTCGAGGC CATCACGCCG CAGACCCTGA
CGAGCGGATG ACCACTCAGG ACGTCGAGGC CATCACGCCG CAGACCCTGA
GGAGCGCATG ACCACTCAGG ACGTCGAGGC GATCACGCCG CAGACGCTGA
CGAGCGGATG ACCACTCAGG ACGTCCAGGC CATCACGCCG CAGACCTTGA
GGAGCGGATG ACCACCCAGG ACGTCGAGGC GATCACGCCG CAGACGCTGA
CGAGCGGATG ACCACGCAGG ACGTCGAGGC CATCACGCCG CAGACCCTGA
GGAACGGATG ACCACTCAGG ACGTCGACGC GATCACGCCG CAGACACTGA
GGAGCGGATG ACCACCCAGG ACGTCGAGGC GATCACGCCG CAGACGCTGA
GGAGCGGATG ACCACCCAGG ACGTCGAGGC GATCACGCCG CAGACGCTGA
GGAGCGGATG ACCACCCAGG ACGTCGAGGC GATCACGCCG CAGACGCTGA
CGACCGCATG ACCACCCAGG ACGTCGAGGC GATCACCCCG CAGACCCTGA
CGAGCGGATG ACCACCCAGG ACGTCGAGGC CATCACGCCG CAGACCCTGA
CGAGCGGATG ACCACCCAGG ACGTCGAGGC CATCACGCCG CAGACCCTGA
TGAGCGCATG ACCACCCAGG ACGTCGACGC GATCACCCCG CAGACCCTGA
CGAGCGCATG ACCACCCAGG ACGTCGAGGC GATCACGCCG CAGACCCTGA
CGAGCGGATG ACCACGCAGG ACGTCGAGGC GATCACGCCG CAGACCCTGA
TGAGCGGATG ACCACCCAGG ACGTCGACGC GATCACGCCG CAGACCCTGA
GGAGCGGATG ACCACCCAGG ACGTCGAGGC GATCACGCCG CAGACGCTGA
TGAGCGGATG ACCACTCAGG ACGTCGAGGC CATCACGCCG CAGACCCTGA
TGAGCGCATG ACCACCCAGG ACGTCGAGGC GATCACGCCG CAGACCCTGA
CGAGCGGATG ACCACCCAGG ACGTCGAGCC GATCACGCCG CAGACCCTGA
CGAGCGGATG ACCACCCAGG ACGTCGAGGC CATCACGCCG CAGACCCTGA
CGAGCGGATG ACCACCCAGG ACGTCGAGGC GATCACGCCG CAGACCCTGA
CGAGCGGATG ACCACCCAGG ATGTCGAGGC GATCACGCCG CAGACCCTGA
GGAGCGGATG ACCACCCAGG ACGTGGAGGC GATCACACCG CAGACGTTGA
GGAGCGGATG ACCACCCAGG ATGTCGAGGC GATCACGCCG CAGACGCTGA
CGAGCGGATG ACCACCCAGG ACGTCGAGGC GATCACTCCG CAGACCCTGA
CGAGCGGATG ACCACTCAGG ACGTCGAGGC GATCACCCCG CAGACCTTGA

CGACCGCATG ACCACTCAGG ATGCTGAGTC GATCACCCCT ACCTCGCTGA
GGAACGGATG ACCACCCAGG ACGTCGAGGC CATCACTCCG CAGACCCTGA
CGAGCGCATG ACGACTCAGG ACGTCGAGGC GATCACGCCG CAGACCCTGA
```

FIG. 1D

```
          130        140        150        160        170
     TCAACATCCG TCCCGTCGTG GCGGCGATCA AGGAGTTCTT CGGAACCAGC
     TCAACATCCG GCCGGTGGTC GCCGCGATCA AGGAGTTCTT CGGCACCAGC
     TCAACATCCG GCCGGTCGTT GCCGCGATCA AGGAGTTCTT CGGCACCAGC
     TCAACATCCG TCCCGTCGTG GCGGCGATCA AGGAGTTCTT CGGCACGTCG
     TCAACATCCG TCCCGTCGTG GCGGCGATCA AGGAGTTCTT CGGCACCAGC
     TCAACATCCG GCCGGTGGTC GCCGCGATCA AGGAGTTCTT CGGCACCAGC
     TCAACATCCG GCCGGTGGTC GCCGCGATCA AGGAGTTCTT CGGCACCAGC
     TCAACATCCG TCCCGTCGTG GCGGCGATCA AGGAGTTCTT CGGCACCAGC
     TCAACATCCG TCCCGTCGTG GCGGCCATCA AGGAGTTCTT CGGCACCAGC
     TCAACATCCG TCCCGTCGTG GCGGCGATCA AGGAGTTCTT CGGAACCAGC
     TCAACATCCG TCCCGTCGTG GCGGCGATCA AGGAGTTCTT CGGCACCAGC
     TCAACATCCG TCCCGTGGTG GCGGCGATCA AGGAGTTCTT CGGGACCAGC
     TCAACATCCG TCCCGTCGTG GCGGCGATCA AGGAGTTCTT CGGTACGTCG
     TCAACATCCG TCCCGTCGTG GCGGCGATCA AGGAGTTCTT CGGAACGTCG
     TCAACATCCG TCCCGTCGTG GCGGCGATCA AGGAGTTCTT CGGAACGTCG
     TCAACATTCG CCCCGTGGTC GCCGCCATTA AGGAGTTCTT CGGCACCAGC
     TCAACATCCG TCCGGTTGTG GCCGCGATCA AGGAGTTCTT CGGCACCAGC
     TCAACATCCG GCCGGTCGTC GCCGCGATCA AGGAGTTCTT CGGCACCAGC
     TCAATATCCG GCCGGTGGTG GCCGCGATCA AGGAGTTCTT CGGCACCAGC
     TCAACATCCG GCCGGTGGTC GCCGCGATCA AGGAGTTCTT CGGCACCAGC
     TCAACATCCG GCCGGTCGTC GCCGCGATCA AGGAGTTCTT CGGCACCAGC
     TCAACATCCG GCCGGTCGTC GCCGCGATCA AGGAGTTCTT CGGCACCAGC
     TCAACATCCG CCCGGTGGTC GCCGCCATCA AGGAGTTCTT CGGCACCAGC
     TCAATATCCG TCCGGTGGTC GCCGCTATCA AGGAATTCTT CGGCACCAGC
     TCAACATCCG GCCGGTGGTC GCCGCGATCA AGGAGTTCTT CGGCACCAGC
     TCAACATCCG TCCGGTCGTT GCGGCGATCA AGGAGTTCTT CGGAACCAGC
     TCAACATCCG TCCCGTCGTG GCGGCGATCA AGGAGTTCTT CGGGACCAGC
     TCAACATCCG CCCGGTGGTC GCCGCCATCA AGGAATTCTT CGGCACCAGC
     TCAACATCCG TCCCGTCGTG GCGGCGATCA AGGAGTTCTT CGGCACCAGC
     TCAACATCCG CCCCGTCGTG GCGGCGATCA AGGAGTTCTT CGGCACCAGC
     TCAACATCCG TCCCGTCGTG GCGGCGATCA AGGAGTTCTT CGGCACCAGC
     TCAACATCCG GCCGGTCGTG GCCGCGATCA AGGAGTTCTT CGGCACCAGC
     TCAACATCCG TCCCGTCGTG GCGGCGATCA AGGAGTTCTT CGGTACCAGC
     TCAACATCCG TCCGGTCGTT GCCGCGATCA AGGAGTTCTT CGGAACCAGC
     TCAACATCCG TCCCGTTGTG GCCGCGATCA AGGAGTTCTT CGGCACCAGC
     TCAACATCCG TCCCGTCGTG GCCGCGATCA AGGAGTTCTT CGGCACCAGC
     TCAACATCCG GCCCGTCGTC GCCGCGATCA AGGAGTTCTT CGGCACCAGC
     TCAACATCCG CCCGGTGGTC GCCCCGATCA AGGAGTTCTT CGGCACCAGC
     TCAACATCCG CCCCGTCGTG GCGGCGATCA AGGAGTTCTT CGGCACCAGC
     TCAACATCCG CCCGGTGGTC GCCGCGATCA AGGAGTTCTT CGGCACCAGC
     TCAACATCCG GCCCGTGGTC GCCGCATCA AGGAGTTCTT CGGCACCAGC
     TCAACATCCG TCCGGTCGTT GCCGCGATCA AGGAGTTCTT CGGAACCAGC
     TCAACATCCG TCCCGTCGTG GCGGCGATCA AGGAATTCTT CGGCACCAGC
     TCAACATCCG CCCCGTGGTG GCCGCGATCA AGGAGTTCTT CGGCACCAGC

TCAACGTTCG CCCTGTTTCT GCCGCCATCC GCGAGTTCTT CGGAACCTCA
     TCAACATCCG TCCGATCACG GCGGCGCTCC GGGAGTTCTT CGGCACCTCA
     TCAACATCCG CCCGGTCGTC GCCGCGATCA AGGAGTTCTT CGGAACCTCC
```

FIG. IE

```
      180        190        200        210        220
CAGCTGTCGC AGTTCATGGA CCAGAACAAC CCGCTGTCGG GCCTGACCCA
CAGCTGAGCC AATTCATGGA CCAGAACAAC CCGCTGTCGG GGTTGACCCA
CAGCTCTCGC AGTTCATGGA CCAGAACAAC CCGCTTTCGG GTCTGACCCA
CAGCTGTCGC AGTTCATGGA CCAGAACAAC CCGCTGTCGG GTCTGACCCA
CAGCTGTCCC AGTTCATGGA CCAGAACAAC CCGCTGTCGG GGCTCACCCA
CAGCTGAGCC AATTCATGGA CCAGAACAAC CCGCTGTCGG GGTTGACCCA
CAGCTGAGCC AATTCATGGA CCAGAACAAC CCGCTGTCGG GGTTGACCCA
CAGCTCTCGC AGTTCATGGA CCAGAACAAC CCGCTGTCCG GGCTGACCCA
CAGCTCTCGC AGTTCATGGA CCAGAACAAC CCATTGTCCG GGCTGACCCA
CAGCTGTCGC AGTTCATGGA CCAGAACAAC CCGCTTTCGG GTCTGACCCA
CAGCTGTCGC AGTTCATGGA CCAGAACAAC CCGCTGTCCG GGCTGACCCA
CAGCTGTCGC AGTTCATGGA CCAGAACAAC CCGCTGTCGG GCCTGACCCA
CAGCTGTCGC AGTTCATGGA CCAGAACAAC CCGCTGTCGG GTCTGACCCA
CAGCTGTCGC AGTTCATGGA TCAGAACAAC CCGCTGTCGG GTCTGACCCA
CAGCTGTCGC AGTTCATGGA TCAGAACAAC CCGCTGTCGG GTCTGACCCA
CAGCTGTCGC AGTTCATGGA CCAGAACAAC CCGCTGTCGG GCCTGACCCA
CAGCTCTCGC AGTTCATCGA CCAGAACAAC CCGCTGTCAG GTCTCACCCA
CAGCTCTCGC AGTTCATGGA CCAGAACAAC CCGCTGTCGG GTCTGACCCA
CAGCTGTCGC AGTTCATGGA CCAGAACAAC CCGCTGTCCG GCCTAACCCA
CAGCTCTCGC AGTTCATGGA CCAGAACAAC CCGCTGTCGG GTCTGACCCA
CAGCTGTCGC AGTTCATGGA CCAGAACAAC CCGCTGTCGG GCCTCACCCA
CAGCTGAGCC AGTTCATGGA CCAGAACAAC CCGCTGTCCG GTCTGACCCA
CAGCTCTCCC AGTTCATGGA CCAGAACAAC CCGCTGTCGG GCCTCACCCA
CAGCTGTCGC AGTTCATGGA TCAGAACAAC CCTCTGTCGG GCCTGACCCA
CAGCTGTCGC AGTTCATGGA CCAGAACAAC CCGCTGTCGG GGCTGACCCA
CAGCTGTCGC AGTTCATGGA CCAGAACAAC CCGCTCTCCG GTCTCACCCA
CAGCTGTCGC AGTTCATGGA CCAGAACAAC CCGCTGTCGG GTCTGACCCA
CAGCTGTCGC AGTTCATGGA CCAGAACAAC CCGCTGTCAG GTCTGACCCA
CAGTTGTCCC AGTTCATGGA CCAGAACAAC CCGCTGTCGG GGCTCACCCA
CAGCTGTCGC AGTTCATGGA CCAGAACAAC CCGCTGTCGG GTCTGACCCA
CAGCTGTCGC AGTTCATGGA CCAGAACAAC CCGCTGTCGG GTCTGACCCA
CAGCTCTCGC AGTTCATGGA CCAGAACAAC CCGCTGTCGG GCCTGACCCA
CAGCTGTCGC AGTTCATGGA CCAGAACAAC CCGCTTTCGG GTCTGACCCA
CAGCTGTCGC AGTTCATGGA CCAGAACAAC CCGCTGTCCG GTCTCACCCA
CAGCTCTCGC AGTTCATGGA CCAGAACAAC CCGCTGTCAG GTCTCACCCA
CAGCTGTCGC AGTTCATGGA CCAGAACAAC CCGCTGTCGG GTCTGACCCA
CAGCTCTCGC AGTTCATGGA CCAGAACAAC CCGCTCTCCG GTCTGACGCA
CAGCTCTCGC AGTTCATGGA CCAGAACAAC CCGCTGTCGG GTCTGACCCA
CAGCTGAGCC AGTTCATGGA CCAGAACAAC CCGCTGTCGG GTCTGACCCA
CAGCTGTCGC AGTTCATGGA CCAGAACAAC CCGCTGTCCG GGCTGACCCA
CAGCTGAGCC AATTCATGGA CCAGAACAAC CCGCTGTCGG GGTTGACCCA
CAGCTGTCGC AGTTCATGGA CCAGAACAAC CCGCTCTCCG GTCTCACCCA
CAGCTGTCGC AGTTCATGGA-CCAGAACAAC CCGCTGTCGG GTCTGACCCA
CAGCTCTCGG AGTTCATGGA TCAGAACAAC CCGCTGTCGG GGCTCACCCA

CAGCTATCGC AGTTCATCGA CCAGAACAAC TCTCTGTCCG GTCTGACCCA
CAGCTGTCGC AGTTCATGGA CCAAAACAAC CCACTGTCGG GTCTGACCCA
CAGCTGTCGC AGTTCATGGA CCAGAACAAC CCGCTGTCGG GCCTGACCCA
```

FIG. 1F

```
              230        240        250        260        270
         CAAGCGTCGT CTGTCGGCGC TGGGCCCCGG TGGTCTGACC CGTGACCGCG
         CAAGCGCCGA CTGTCGGCGC TGGGCCCCGG CGGTCTGTCA CGTGAGCGTG
         CAAGCGCCGC CTGTCGGCGC TGGGCCCCGG CGGTCTGTCC CGTGAGCGTG
         CAAGCGCCGC CTGTCGGCGC TGGGCCCGGG TGGTCTGTCC CGTGAGCGCG
         CAAGCGCCGC CTGTCGGCGC TGGGCCCGGG TGGTCTGTCC CGGGAGCGGG
         CAAGCGCCGA CTGTCGGCGC TGGGGCCCGG CGGTCTGTCA CGTGAGCGTG
         CAAGCGCCGA CTGTCGGCGC TGGGGCCCGG CGGTCTGTCA CGTGAGCGTG
         CAAGCGGCGC CTGAACGCAC TGGGCCCGGG TGGTCTGTCC CGGGAGCGGG
         CAAGCGTCGC CTGAACGCGC TCGGCCCGGG TGGTCTGTCC CGGGACCGGG
         CAAGCGTCGT CTGTCGGCTC TGGGCCCCGG TGGTCTGACC CGTGACCGCG
         CAAGCGTCGT CTCTCGGCGC TCGGGCCCGG CGGTCTGTCC CGTGAGCGCC
         CAAGCGCCGG CTGTCCGCGC TTGGCCCCGG CGGTCTGTCC CGTGAGCGCG
         CAAGCGCCGC CTGTCGGCGC TGGGCCCCGG TGGTCTGTCC CGTGAGCGCG
         CAAGCGTCGT CTGTCGGCGC TGGGCCCCGG CGGTCTGTCC CGTGAGCGCG
         CAAGCGTCGT CTGTCGGCGC TCGGCCCCGG CGGTCTGTCC CGTGAGCGCG
         CAAGCGCCGG CTTTCGGCGC TGGCCCCGG CGGTCTGTCA CGTGAGCGTG
         CAAGCGCCGG TTGTCGGCGC TGGGGCCGGG CGGTCTGTCC CGTGAGCGGG
         CAAGCGTCGT CTGTCGGCGC TGGGCCCGGG TGGTCTGTCC CGTGAGCGTG
         CAAGCGCCGG CTGTCGGCGC TGGGGCCGGG CGGTCTGTCG CGTGAGCGTG
         CAAGCGTCGT CTGTCGGCGT TGGGCCCCGG TGGTCTGTCG CGTGAGCGTG
         CAAGCGCCGC CTGTCGGCGC TGGCCCCGGC CGGTCTGTCC CGCGAGCGGG
         CAAGCGCCGC CTCTCGGCGC TGGGCCCCGG CGGTCTGTCC CGTGAGCGCG
         CAAGCGCCGG CTTTCGGCGC TGGGGCCGGG CGGTCTGTCC CGGGAGCGTG
         CAAGCGCCGG CTGTCGGCGC TGGGCCCGGG TGGTTTGTCG CGTGAGCGTG
         CAAGCGCCGG CTGTCGGCGC TGGGCCCGGG TGGTCTGTCG CGTGAGCGTG
         CAAGCGCCGG CTGTCGGCGC TGGGGCCGGG CGGTCTGTCC CGTGAGCGCG
         CAAGCGCCGC CTCTCGGCGC TCGGCCCCGG TGGTCTGTCC CGTGAGCGTG
         CAAGCGTCGT CTGTCGGCGC TGGGCCCCGG TGGTCTGTCG CGTGAGCGCG
         CAAGCGGCGT CTGTCGGCGC TGGGCCCCGG TGGTCTGTCG CGGGAGCGTG
         CAAGCGCCGC CTGTCGGCGC TGGGCCCGGG CGGTCTGTCC CGTGAGCGCG
         CAAGCGTCGT CTGTCGGCGC TGGGCCCCGG CGGTCTGTCC CGTGAGCGCG
         CAAGCGCCGC CTGTCGGCGC TGGGCCCGGG CGGTCTGTCC CGTGAGCGCG
         CAAGCGCCGC CTGTCGGCGC TGGGCCCGGG TGGTCTGTCC CGCGAGCGGG
         CAAGCGTCGC CTGTCGGCGC TGGGCCCCGG CGGTCTGTCC CGTGAGCGTG
         CAAGCGCCGC CTCTCGGCGC TGGGGCCGGG CGGTCTGTCC CGTGAGCGTG
         CAAGCGCCGG TTGTCGGCGC TGGGGCCGGG CGGTCTGTCC CGTGAGCGGG
         CAAGCGTCGT CTTTCGGCGC TGGGCCCCGG CGGTCTGTCC CGTGAGCGCG
         CAAGCGGCGT CTGTCCGCTC TGGGGCCGGG CGGTCTGTCC CGTGAGCGGG
         CAAGCGCCGG CTGTCGGCGC TCGGCCCGGG TGGTCTGTCC CGTGAGCGTG
         CAAGCGCCGG CTGTCGGCGC TGGGCCCGGG CGGTCTGAGC CGGGAGCGCG
         CAAGCGCCGG CTGTCGGCGC TGGGGCCCGG CGGCCTCTCC CGGGAGCGGG
         CAAGCGCCGA CTGTCGGCGC TGGGGCCCGG CGGTCTGTCA CGTGAGCGTG
         CAAGCGCCGC CTCTCGGCGC TGGGGCCGGG CGGTCTGTCC CGTGAGCGCG
         CAAGCGTCGC CTGTCGGCGC TGGGCCCCGG CGGTCTGTCC CGTGAGCGCG
         CAAGCGGCGG CTCTCGGCGC TTGGTCCGGG CGGTCTGTCG CGCGAGCGGG

CAAGCGTCGT CTCTCCGCAC TGGGCCCAGG TGGCCTGTCG CGTGAGCGCG
         CAAGCGTCGA CTCTCGGCGC TGCGGCCCGG TGGTCTGTCC CGTGAGCGCG
         CAAGCGTCGT CTGTCGGCGC TGGGCCCCGG CGGTCTGTCC CGTGAGCGCG
```

FIG. IG

```
            280        290        300
F   CCGGCCTCGA GGTCCGCGAC GTGCACCCCT CGCACT (SEQ ID NO:1)
|   CCGGGCTGGA GGTCCGCGAC GTGCACCCGT CGCACT (SEQ ID NO:2)
|   CCGGCCTGGA AGTGCGTGAC GTGCACCCCT CGCACT (SEQ ID NO:3)
|   CCGGCCTCGA GGTCCGCGAC GTGCACTCCA GCCACT (SEQ ID NO:4)
|   CCGGGCTGGA GGTCCGCGAC GTGCACCCGT CCCACT (SEQ ID NO:5)
|   CCGGGCTGGA GGTCCGCGAC GTGCACCCGT CGCACT (SEQ ID NO:6)
|   CCGGGCTGGA GGTCCGCGAC GTGCACCCGT CGCACT (SEQ ID NO:7)
|   CGGGCCTCGA GGTGCGCGAC GTGCACCCGA GTCACT (SEQ ID NO:8)
|   CCGGCCTGGA GGTCCGCGAC GTGCACCCGA GCCACT (SEQ ID NO:9)
|   CTGGCCTTGA GGTCCGCGAC GTGCACCCCT CGCACT (SEQ ID NO:10)
|   CCGGTCTCGA GGTTCGTGAC GTGCACCCGT CGCACT (SEQ ID NO:11)
|   CCGGCCTGGA GGTCCGCGAC GTGCACGCCA GCCACT (SEQ ID NO:12)
|   CCGGCCTCGA AGTCCGTGAC GTGCACCCGT CGCACT (SEQ ID NO:13)
|   CCGGCCTTGA GGTCCGCGAC GTCCACTCGT CGCACT (SEQ ID NO:14)
|   CCGGCCTTGA GGTCCGCGAC GTCCACTCGT CGCACT (SEQ ID NO:15)
|   CCGGGCTGGA GGTCCGCGAC GTGCACCCGT CGCACT (SEQ ID NO:16)
|   CGGGCCTCGA GGTCCGCGAC GTGCACCCGT CTCACT (SEQ ID NO:17)
|   CGGCTCTGGA AGTACGTGAC GTGCACCCGT CGCACT (SEQ ID NO:18)
|   CCGGGCTAGA GGTCCGCGAC GTGCACCCGT CGCACT (SEQ ID NO:19)
|   CCGGGCTGGA AGTCCGTGAC GTGCACCCGT CGCACT (SEQ ID NO:20)
|   CCGGCCTCGA GGTCCGCGAC GTGCACCCGA ACCACT (SEQ ID NO:21)
|   CCGGCCTGGA GGTCCGTGAC GTCCACCCCT CGCACT (SEQ ID NO:22)
|   CCGGGCTGGA AGTGCGTGAC GTGCACCCGT CGCACT (SEQ ID NO:23)
|   CCGGGCTAGA GGTCCGTGAC GTGCACCCTT CGCACT (SEQ ID NO:24)
|   CCGGCTTGGA GGTCCGTGAC GTGCACCCGT CGCACT (SEQ ID NO:25)
|   CCGGTCTGGA AGTTCGTGAC GTGCACCCGT CGCACT (SEQ ID NO:26)
|   CCGGACTTGA GGTCCGCGAC GTGCACTCCA GCCACT (SEQ ID NO:27)
|   CCGGCCTGGA AGTTCGTGAC GTGCACCCGT CCCACT (SEQ ID NO:28)
|   CCGGGCTGGA GGTCCGCGAC GTGCACCCGT CCCACT (SEQ ID NO:29)
|   CCGGCCTTGA GGTCCGCGAC GTGCACTCCA GCCACT (SEQ ID NO:30)
|   CCGGCCTCGA GGTCCGCGAC GTGCACCACA GCCACT (SEQ ID NO:31)
|   CCGGGCTGGA GGTCCGGGAC GTGCACCCGT CGCACT (SEQ ID NO:32)
|   CCGGCCTTGA GGTCCGCGAC GTGCACGCCA GCCACT (SEQ ID NO:33)
|   CCGGGCTGGA AGTTCGTGAC GTGCACCCGT CGCACT (SEQ ID NO:34)
|   CGGGCCTCGA GGTCCGCGAC GTGCACCCGT CGCACT (SEQ ID NO:35)
|   CTGGCCTCGA GGTCCGCGAC GTGCACCCCA GCCACT (SEQ ID NO:36)
|   CCGGGCTGGA GGTCCGTGAC GTGCACCCGT CGCACT (SEQ ID NO:37)
|   CCGGGCTTGA GGTCCGTGAC GTGCACCCGT CCCACT (SEQ ID NO:38)
|   CCGGCCTCGA GGTCCGCGAC GTCCACCCGT CGCACT (SEQ ID NO:39)
|   CCGGGCTGGA GGTCCGCGAC GTGCACCCCA GCCACT (SEQ ID NO:40)
|   CCGGGCTGGA GGTCCGCGAC GTGCACCCGT CGCACT (SEQ ID NO:41)
|   CCGGTCTGGA AGTTCGTGAC GTGCACCCGT CGCACT (SEQ ID NO:42)
|   CCGGCCTCGA GGTCCGCGAC GTGCACTCCA GCCACT (SEQ ID NO:43)
|   CCGGGCTGGA GGTCCGTGAC GTGCACTCGA GCCACT (SEQ ID NO:44)

CCGGCATTGA GGTCCGAGAC GTTCACGCTT CTCACT (SEQ ID NO:45)
|   CCGGCCTGGA AGTCCGCGAC GTGCACCCCT CGCACT (SEQ ID NO:46)
F   CCGGCCTCGA GGTGCGAGAC GTCCACCCGT CGCACT (SEQ ID NO:47)
```

METHOD FOR IDENTIFYING MYCOBACTERIAL SPECIES BY COMPARATIVE SEQUENCE ANALYSIS OF RPOB GENE

BACKGROUND OF THE INVENTION

1. Field of the Invention

The present invention relates to a method for diagnosis of mycobacterial infection by comparative sequence analysis of rpoB gene coding for β-subunit of RNA polymerase, more specifically, to a method for detecting and identifying mycobacterial species which comprises steps of amplifying 342 bp of rpoB gene fragments from clinically isolated mycobacteria using mycobacterial rpoB-specific PCR primers; sequencing 306 bp regions of the amplified 342 bp of rpoB gene fragments except the primer region; and, inferring a phylogenetic tree with reference species.

2. Description of the Prior Art

The genus Mycobacterium covers a wide range of organisms including obligate parasites causing serious human and animal diseases such as tuberculosis, bovine tuberculosis and leprosy, opportunistic pathogens, and saprophytic species found in natural environment (see: Murray, P. R., E. J. Baron, M. A. Pfaller, F. C. Tenover and R. H. Yolken, Manual of Clinical Microbiology, 6th Ed. ASM Press, Washington, D.C., Frederick S. N., B. Metchock, pp. 400–437(1995)).

Recently, in line with rapid increase of AIDS patients worldwide, infections with nontuberculous mycobacteria or mycobacteria other than *Mycobacterium tuberculosis* (hereinafter, referred to as "MOTT") or *Mycobacterium leprae* go on increasing (see: Barnes, P., A. B. Bloch, P. T. Davidson and D. E. Snider, Jr., Tuberculosis in Patients with Immunodeficiency Virus Infection, New Engl. J. Med., 324:1644–1650(1991)).

In general, mycobacteria have been largely classified into four groups depending on growth rate and pigmentation of colonies(see: Runyon, E. H., Identification of Mycobacterial Pathogens Utilizing Colony Characteristics, Am. J. Clin. Pathol., 54:578–586(1970)), and numerical taxonomic analysis(see: Sneath, P. H. A. and R. R. Sokal, Numerical Taxonomy, W.H. Freeman & Co., San Francisco (1973)), immunological techniques (see: Wayne, L. G., R. C. Good, A. Tsang, R. Buttler, D. Dawson, D. Groothuis, W. Gross, J. Hawkins, J. Kilburn, M. Kubin, K. H. Schroder, V. A. Silcox, M.-F. Thorel, C. Woodley and M. A. Yakrus, Serovar Determination and Molecular Taxonomic Correlation in *Mycobacterium avium, Mycobacterium intracellulare*, and *Mycobacterium scrofulaceum*: A Cooperative Study of the international Working Group on Mycobacterial Taxonomy, Int. J. Syst. Bacteriol., 43(3):482–489(1993)), comparison of cell wall composition, DNA-DNA homology, and analysis employing restriction endonucleases (see: Telenti, A., F. Marchesi, M. Balz, F. Bally, E. C. Botter and T. Bodmer, Rapid Identification of Mycobacteria to the Species Level by Polymerase Chain Reaction and Restriction Enzyme Analysis, J. Clin. Microbiol., 31(2):175–178(1993)) have been used to classify mycobacterial species more definitely.

However, the conventional methods for identifying mycobacterial species have revealed disadvantages that they are laborious and complex, and require so long time. Naturally, alternative methods for identification employing a gene as a marker, e.g., genus-specific or species-specific PCR primers or nucleic acid probe against a specific gene have been used in the art.

Under the circumstances, mycobacterial phylogenetic analysis to provide a criterion of differentiation and identification of mycobacterial species has been performed based on the sequences of 16S rRNA or its coding gene (16S rDNA), which provided a fact that 16S rRNA-based phylogenetic analysis permits to define mycobacterial phylogenetic relationships well (see: Stahl, D. A. and J. W. Urbance, The Division between Fast and Slow-growing Species Corresponds to Natural Relationships among the Mycobacteria, J. Bacteriol., 172:116–124(1990); Rogall, T., T. Flohr and E. C. Bottger, Differentiation of Mycobacterium Species by Direct Sequencing of Amplified DNA, J. Gen. Microbiol., 136(Pt9):1915–1920(1990); Rogall, T., J. Wolters, T. Flohr and E. C. Bottger, Towards a Phylogeny and Definition of Species at the Molecular Level within the Genus Mycobacterium, Int. J. Syst. Bacteriol., 40:323–330(1990)).

However, 16S rRNA-based phylogenetic analysis has a shortcoming that clear definition of species boundaries is often difficult (for example, in the case of slow-growing mycobacteria) (see: Fox, G. E., J. D. Wisotzkey and P. J. Jurtshumk, How Close IS Close: 16S rRNA Sequence Identitiy May Not Be Sufficeint to Guarantee Species Identity, Int. J. Syst. Bacteriol., 42:166–170(1992)).

Thus, a dnaJ gene coding for a stress protein has been suggested as a promising alternative (see: Takewaki, S. K. Okuzumi, H. Ishiko, K. Nakahara, A. Ohkubo and R. Nagai, Genus-specific Polymerase Chain Reaction for the Mycobacterial dnaj Gene and Species-specific Oligonucleotide Probes, J. Clin. Microbiol., 31:446–450(1993); Takewaki, S., K. Okuzumi, I. Manabe, M. Tanimura, K. Miyamura, K. Nakahara, Y. Yazaki, A. Ohkubo and R. Nagai, Nucleotide Sequence Comparison of the Mycobacterial dnaJ Gene and PCR-restriction Fragment Length Polymorphism Analysis for Identification of Mycobacterial Species, Int. J. Syst. Bacteriol., 44:159–166(1994)). However, it was found that dnaJ-based phylogenetic analysis has several problems unsuitable for differentiation of rapid-growing mycobacteria.

The said nucleic acid probes to employ 16S rRNA gene as a marker are clear criteria for defining 5 kinds of mycobacterial species, e.g., *M. tuberculosis, M. bovis*, MAC, *M. kansasii* and *M. gordonae*, and they are commercially available in the art (AccuProbe: Gen-Probe, San Diego, Calif., USA) (see: Nolte, F. S. and Beverly Metchock, Ch. 31. Mycobacterium in Manual of Clinical Microbiology, pp. 400–437(1995)).

Also, IS6110 insertion element which exists in TB complex (*M. tuberculosis, M. africanum* and *M. bovis*) in multiple copies, has been employed as a marker in a PCR detection method. However, the result obtained through the said method maybe false negative, since *Mycobacterium tuberculosis* free of the insertion element has been reported (see: Yuen, L. K., B. C. Ross, K. M. Jackson and B. Dwyer, Characterization of *Mycobacterium tuberculosis* Strains from Vietnamese Patients by Southern Blot Hybridization, J. Clin. Microbiol., 31:1615–1618(1993)). Primers to amplify the said gene are commercially available now (TB-CR, TB Detection kit, Bioneer Co., Korea), though they play a limited role of detecting mycobacterial species, and can not practically be applied in identifying mycobacteria as well as detecting existence of mycobacteria.

When the afore-mentioned 5 kinds of probes are used, typical mycobacterial species causing human diseases can be identified. However, the probes have a shortcoming of cross-hybridization with newly described species (see: Buttler, W. R., S. P. O'connor, M. A. Yakrus and W. M. Gross, Cross-reactivity of Genetic Probe for Detection of *Mycobacterium tuberculosis* with Newly Described Species

*Mycobacterium celatum*, J. Clin. Microbiol., 32(2):536–538 (1994)). Also, infections with MOTT other than *Mycobacterium tuberculosis* increase, MAIS (*Mycobacterium avium-intracellulare-scrofulaceum*) complex among MOTT infects human frequently, and infections with new species have been reported continuously. Accordingly, there are strong reasons for clear definition of species causing diseases to prevent and control the diseases, and development of a novel nucleic acid probe showing species-specific genetic difference is strongly required in the art.

Under the circumstances, the present inventors have investigated whether a rpoB gene coding for β-subunit of RNA polymerase is useful as a criterion for mycobacterial phylogenetic analysis, based on the following reports:

RNA polymerase gene, besides the said criteria for phylogenetic analysis, can be used as an alternative of 16S rRNA gene, since RNA polymerase has subunits of rpoA, rpoB, rpoc and rpoD which are highly conserved throughout procaryotes (see: Lill, U. I., E. M. Behrendt and G. R. Hartmann, Eur. J. Biochem., 52:411–420(1975)).

Among the subunits, the rpoB gene coding for β-subunit of RNA polymerase is related to rifampin resistance in *Escherichia coli* (see: Jin, D. and C. A. Gross, Mapping and Sequencing of Mutations in the *Escherichia coli* rpoB Gene that Lead to Rifampicin Resistance, J. Mol. Biol., 202:45–58 (1988)), *Mycobacterium tuberculosis* (see: Telenti, A., P. Imboden, F. Marchesi, D. Lowrie, S. Cole, M. J. Colston, L. Matter, K. Schopfer and T. Bodmer, Detection of Rifampin-resistance Mutations in *Mycobacterium tuberculosis*, Lancet, 341:647–650(1993)), *Mycobacterium leprae* (see: Honore, N. T., Bergh, S., Chanteau, S., Doucet-Populaire, F., Eiglmeier, K., Garnier, T., Georges, C., Launois, P., Limpaiboon, T., Newton, S., Niang, K., Del Portillo, P., Ramesh, G. R., Reddi, P., Ridel, P. R., Sittisombut, N., Wu-Hunter, S. and Cole, S. T., Nucleotide Sequence of the First Cosmid from the *Mycobacterium leprae* Genome Project: Structure and Function of the Rif-Str Regions, Mol. Microbiol., 7(2):207–214(1993)) and *M. smegmatis* (see: Levin, M. E. and Hatfull, G. F., *Mycobacterium smegmatis* RNA Polymerase: DNA Supercoiling, Action of Rifampin and Mechanism of Rifampin Resistance, Mol. Microbiol., 8(2):277–285(1993)).

Also, nucleotide sequence in a region of a rpoB gene is highly conserved in some mycobacteria other than *Mycobacterium tuberculosis* (see: Hunt, J. M., G. D. Roberts, L. Stockman, T. A. Felmiee and D. H. Persing, Detection of a Genetic Locus Encoding Resistance to Rifampin in Mycobacterial Cultures and in Clinical Specimens, Diagn. Microbiol. Infect. Dis., 18:219–272(1994); Whelen, A. C., T. A. Felmlee, J. M. Hunt, D. L. Williams, G. D. Roberts, L. Stockman and D. H. Persing, Direct Genotypic Detection of *Mycobacterium tuberculosis* Rifampin Resistance in Clinical Specimens by Using Single-tube Heminested PCR, J. Clin. Microbiol., 33:556–561(1995)).

In addition, a rpoB gene is used for phylogenetic establishment of Archaebacteria(see: Puhler, G., H. Leffers, F. Gropp, P. Palm, H. P. Klenk, F. Lottspeich, R. A. Garrett and W. Zillig, Archaebacterial DNA-dependent RNA Polymerases Testify to the Evolution of the Eukaryotic Nuclear Genome, Proc. Natl. Acad. Sci., U.S.A., 86:4569–4573 (1989); Iwabe N., K. Kuma, H. Kishino, M. Hasegawa, and Miyata, Evolution of RNA Polymerases and Branching Patterns of the Three Major Groups of Archaebacteria, J. Mol. Evol., 32:70–78(1991); Klenk, H. P. and W. Zillg, DNA-dependent RNA Polymerase Subunit B as a Tool for Phylogenetic Reconstructions: Branching Topology of the Archaeal Domain, J. Mol. Evol., 38:420–432(1994); Zillig, W., H. P. Klenk, P. Palm, G. Puhler, F. Gropp, R. A. Garrett and H. Leffers, The Phylogenetic Relations of DNA-dependent RNA Polymerases of Archaebacteria, Eukaryotes, and Eubacteria, Can. J. Microbiol., 35:73–80 (1989)), Eubacteria other than *Staphylococcus aureus* (see: Rowland G. C., M. Aboshkiwa and G. Coleman, Comparative Sequence Analysis and Predicted Phylogeny of the DNA-dependent RNA Polymerase Beta Subunits of *Staphylococcus aureus* and other Eubacteria, Biochem. Soc. Trans., 21:40S(1993)) and Plasmodium (see: Gardner, M. J., N. Goldman, P. Barnett, P. W. Moore, K. Rangachari, M. Strath, A. Whyte, D. H. Williamson and R. J. Wilson, Phylogenetic Analysis of the rpoB Gene from the Plastid-like DNA of *Plasmodium falciparum*, Mol. Biochem. Parasitor., 66:221–231(1994)).

SUMMARY OF THE INVENTION

The present inventors investigated whether a rpoB gene can be used as a criterion for mycobacterial phylogenetic analysis: That is, 342 bp of rpoB gene fragments, which corresponds to an amino acid sequence from 447th amino acid to 561st amino acid in *E. coli*, were amplified from 44 mycobacterial species, and 306 bp of nucleotide sequences except for primer sequences were determined and compared with each other. As a result, it was found that: rpoB sequences from the 44 mycobacterial species provide a basis for systematic phylogenetic relationship that can be used to identify clinically isolated mycobacteria which are pathogenic or potentially so; and, therefore, PCR-mediated sequence analysis of rpoB DNA can be regarded as a reliable and rapid method for the diagnosis of mycobacterial infection.

A primary object of the invention is, therefore, to provide a pair of PCR primers which specifically amplify rpoB gene fragments of bacterial species belonging to the genus Mycobacterium.

The other object of the invention is to provide species-specific nucleotide sequences of the rpoB gene fragments amplified by using the said PCR primers.

Another object of the invention is to provide a method for detecting and identifying various mycobacterial species by PCR-mediated sequencing of the rpoB gene fragments amplified from clinical isolates and determining phylogenetic relationship to the reference species.

BRIEF DESCRIPTION OF THE DRAWINGS

The above and the other objects and features of the present invention will become apparent from the following descriptions given in conjunction with the accompanying drawings, in which:

FIGS. 1A–G show nucleotide sequences of the rpoB gene fragments(306 bp) of 44 mycobacterial species and 3 phylogenetically related non-mycobacterial species (SEQ ID NO:1 to SEQ ID NO:47), which were amplified by employing genus Mycobacterium-specific PCR primers.

DETAILED DESCRIPTION OF THE INVENTION

Figure 2A:
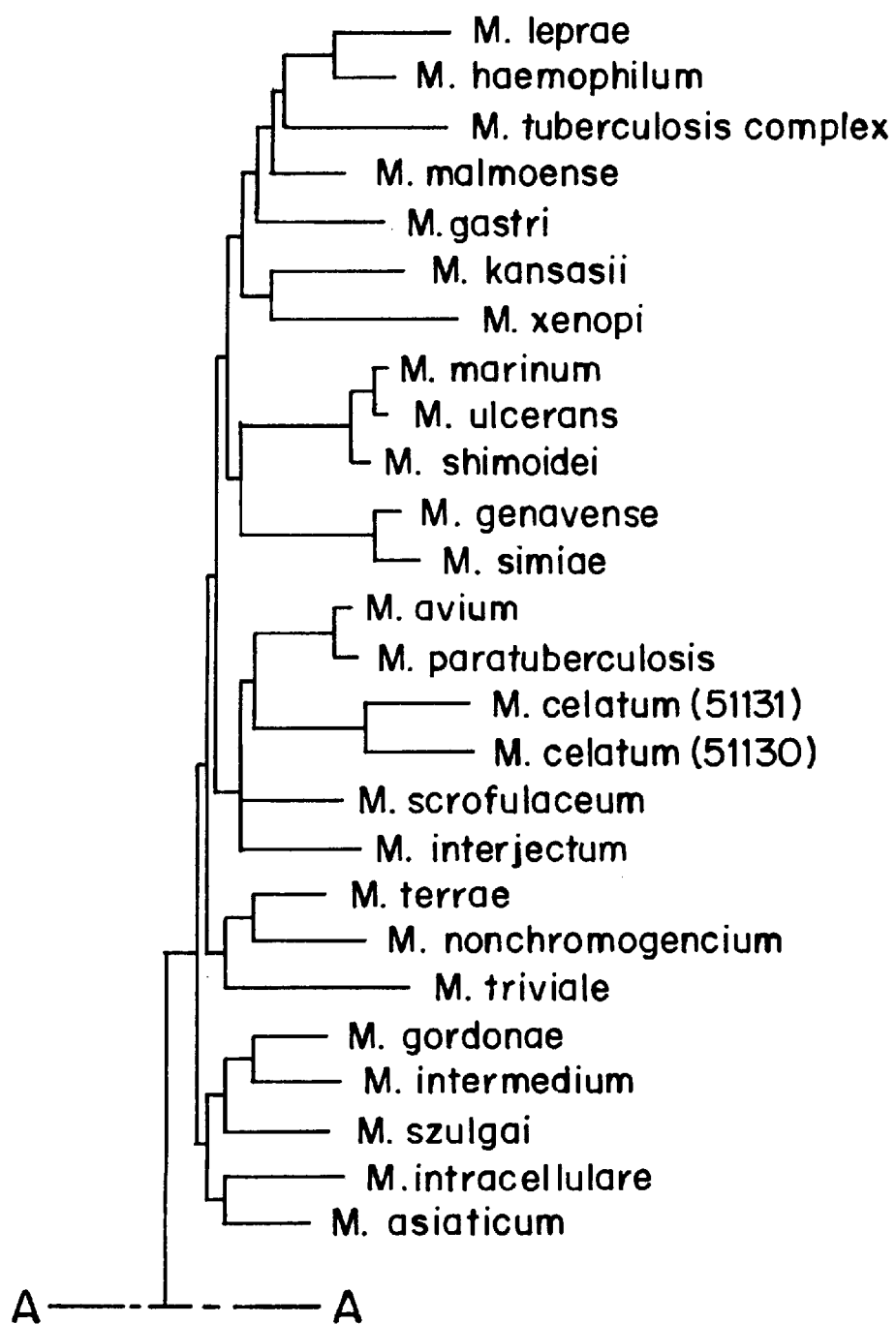
FIGS. 2A–B show a phylogenetic tree based on the nucleotide sequences of the rpoB gene fragments (306 bp) of the 44 mycobacterial species and non-mycobacterial species.

Based on the previous reports that a nucleotide sequence in a region of a rpoB gene is highly conserved in mycobacteria, the present inventors first designed a pair of primers(5'-CGACCACTTCGGCAACCG-3' (SEQ ID NO:48) and 5'-TCGATCGGGCACATCCGG-3' (SEQ ID NO:49)) by which rpoB DNAs of bacteria belonging to genus Mycobacterium can be specifically amplified. Then, amplification of 342 bp of rpoB gene fragments from 44 mycobacterial species including *M. tuberculosis* were followed by employing polymerase chain reaction (PCR). In this connection, 342 bp of rpoB gene fragments from 3 kinds of non-mycobacteria including *Corynebacterium diphtheriae, Nocardia nova* and *Rhodococcus equi* which are phylogenetically related to mycobacteria were also amplified by using the said primers for further use as reference microorganisms to construct a phylogenetic tree. In addition, *Staphylococcus aureus, Bacillus subtilis* and *E. coli* were used as general bacteria for PCR. And then, the nucleotide sequences of the amplified rpoB gene fragments (306 bp) except the said primer sequences were determined, which revealed that there are species-specific nucleotide sequences which are not appeared in non-mycobacteria.

A phylogenetic tree was constructed, based on the total 50 rpoB nucleotide sequences which includes 44 mycobacterial species, 3 kinds of non-mycobacteria which are phylogenetically related to mycobacteria and 3 kinds of general bacteria. The phylogenetic tree provided an alternative for the conventional ambiguous mycobacterial systematics and, revealed that the comparative sequence analysis of the rpoB gene fragments (342 bp) can be used for characterization of mycobacteria. That is, slow- and rapid-growing mycobacteria were clearly identified, and each mycobacterial species was characterized as a distinct entity in the phylogenetic tree. In particular, pathogenic *M. kansasii* were easily distinguished from nonpathogenic *M. gastri*, although they have not been identified by a conventional 16S rRNA sequences. Members of MAC(or MAIS complex) such as *M. avium, M. intracellulare* and *M. scrofulaceum*, which have been regarded as phylogenetically related to the other were also clearly identified. By inferring the phylogenetic tree on the basis of reference species and using the rpoB sequences thus determined, clinical isolates could easily be identified.

Further, *M. leprae*, not yet cultivated in vitro was successfully identified by the procedure punch biopsy-PCR-rpoB sequence analysis.

Accordingly, the amplification of rpoB DNA followed by automated sequencing and the analysis of phylogenetic relationships can be used efficiently to detect and identify clinical isolates of mycobacteria which have not been identified by the conventional methods. In particular, this approach is useful for slowly growing, fastidious or uncultivable mycobacteria. Furthermore, in the case of *M. tuberculosis*, rifampin susceptibility can be simultaneously determined.

The present invention is further illustrated in the following examples, which should not be taken to limit the scope of the invention.

EXAMPLE 1

Isolation of DNA from Various Mycobacterial Strains

*M. leprae* (Thai 53 strain) was prepared from the footpad of nude mice (nu/nu in Balb/c, BTK, U. K.), which was inoculated and maintained for 18 months. A punch biopsy specimen was obtained from an active lesion of a patient diagnosed on the basis of histological findings, AFB staining, and amplification of DNA encoding 18 kDa protein (see: Williams, D. L., T. P. Gillis, R. J. Booth, D. Looker and J. D. Watson, The Use of a Specific DNA Probe and Polymerase Chain Reaction for the Detection of *Mycobacterium leprae*, J. Infect. Dis., 162:193–200(1990)). The resected swollen footpads and biopsy specimen were homogenized in 2 ml phosphate buffered saline (PBS) using Mickle homogenizer (Mickle Laboratory Engineering, Surrey, U.K.). Supernatant was collected after settling down of tissue debris (1×g for 5 min) and *M. leprae* DNA was prepared by the aid of freezing-thawing technique. Other mycobacterial genomic DNAs were prepared by the Bead-beat/Phenol extraction method. A loopful culture of each mycobacteria was suspended with 200 µl of TEN buffer(10 mM Tris-HCl, 1 mM EDTA, 100 mM NaCl) placed in a 2.0 ml screw-cap microcentrifuge tube filled with 100 µl (packed volume) of beads (glass bead, diameter 0.1 mm; Biospec Products, Bartlesville, Okla., U.S.A.) and 100 µl phenol:chloroform:isopropylalcohol solution (50:49:1, v/v/v). To disrupt the bacteria, the tube was oscillated on a Mini-Bead beater (Biospec Products, Bartlesville, Okla., U.S.A.) for one minute, and to separate phases, the tube was centrifuged (12,000×g, 5 min). After the aqueous phase was transferred into another clean tube, 10 µl 3M sodium acetate and 250 µl ice-cold ethanol were added and, the mixture was kept at −20° C. for 10 minutes to precipitate the DNA. The DNA pellet was washed with 70% ethanol, solubilized with 60 µl TE buffer(10 mM Tris-HCl, 1 mM EDTA) and used as a template DNA for PCR for nucleotide sequencing in the following Examples. In this connection, the mycobacterial strains used for the extraction of genomic DNA are shown in Table 1 below, which were provided by American Type Culture Collection (ATCC), the Korean Institute of Tuberculosis, the Korean National Tuberculosis Association (KNTA), etc. 3 kinds of non-mycobacteria including *Corynebacterium diphtheriae, Nocardia nova* and *Rhodococcus equi* which are phylogenetically related to mycobacteria were used as references to construct a phylogenetic tree (see: Table 1), and *Staphylococcus aureus, Bacillus subtilis* and *E. coli* were used as general bacteria for PCR.

TABLE 1

44 Kinds of Mycobacteria and 3 Kinds of Non-mycobacteria Used for Comparative Sequence Analysis of rpoB Gene

| Species | Strain | Source* |
|---|---|---|
| M. abscessus | CAP97E-03 | CPSNU |
| M. africanum | ATCC 25420 | ATCC |
| M. asiaticum | ATCC 25276 | ATCC |
| M. aurum | ATCC 23366 | ATCC |
| M. avium | ATCC 25291 | ATCC |
| M. bovis | ATCC 19210 | ATCC |
| M. bovis BCG | French strain1173P2 | KNTA |
| M. celatum Type 1 | ATCC 51131 | ATCC |
| M. celatum Type 2 | ATCC 51130 | ATCC |
| M. chelonae | ATCC 35749 | ATCC |
| M. chitae | ATCC 19627 | ATCC |
| M. fallax | ATCC 35219 | ATCC |
| M. flavescense | ATCC 14474 | ATCC |
| M. fortuitum | ATCC 6841 | ATCC |
| M. fortuitum 49403 | ATCC 49403 | ATCC |
| M. gastri | ATCC 15754 | ATCC |
| M. genavense | ATCC 51233 | ATCC |
| M. gordonae | ATCC 14470 | ATCC |
| M. haemophilum | ATCC 29548 | ATCC |
| M. interjectum | ATCC 51457 | ATCC |
| M. intermedium | ATCC 51848 | ATCC |
| M. intracellulare | ATCC 13950 | ATCC |
| M. kansasii | ATCC 12478 | ATCC |
| M. leprae | Thai 53 strain | ICD |

TABLE 1-continued

44 Kinds of Mycobacteria and 3 Kinds of Non-mycobacteria Used for Comparative Sequence Analysis of rpoB Gene

| Species | Strain | Source* |
|---|---|---|
| M. malmoense | ATCC 29571 | ATCC |
| M. marinum | ATCC 927 | ATCC |
| M. neoaurum | ATCC 25795 | ATCC |
| M. nonchromogenicum | ATCC 19530 | ATCC |
| M. paratuberculosis | ATCC 19698 | ATCC |
| M. phlei | ATCC 11758 | ATCC |
| M. peregrinum | ATCC 14467 | ATCC |
| M. scrofulaceum | ATCC 19981 | ATCC |
| M. senegalense | ATCC 35796 | ATCC |
| M. shimoidei | ATCC 27962 | ATCC |
| M. simiae | ATCC 25275 | ATCC |
| M. smegmatis | ATCC 19420 | ATCC |
| M. szulgai | ATCC 35799 | ATCC |
| M. terrae | ATCC 15755 | ATCC |
| M. thermoresistibile | ATCC 19527 | ATCC |
| M. triviale | ATCC 23292 | ATCC |
| M. tuberculosis H37Rv | ATCC 27294 | ATCC |
| M. ulcerans | ATCC 19423 | ATCC |
| M. vaccae | ATCC 15483 | ATCC |
| M. xenopi | ATCC 19250 | ATCC |
| R. equi | ATCC 10146 | ATCC |
| N. nova | ATCC 21197 | ATCC |
| C. diphtheriae | SNUMCd | IMSNU |

*KNTA: The Korean Institute of Tuberculosis, Korean National Tuberculosis Association
ICD: The Institute of Chronic Diseases, College of Medicines, Catholic University
CPSNU: Department of Clinical Pathology, College of Medicines, Seoul National University
IMSNU: Culture Collection Center, Institute of Microbiology, Seoul National University

EXAMPLE 2

PCR Amplification of rpoB Gene Fragments

Based on the report that a nucleotide sequence in a region of a rpoB gene is highly conserved in mycobacteria, a pair of primers specific to the genus Mycobacterium were designed as followings:

MF primer: 5'-CGACCACTTCGGCAACCG-3' (SEQ ID NO:48)

MR primer: 5'-TCGATCGGGCACATCCGG-3' (SEQ ID NO:49)

And then, 50 ng of genomic DNA of each bacterium isolated in Example 1 and 20 pmole of the said primers were added to a PCR mixture tube (Pre-mix Top, Bioneer, Korea), and distilled water was added in a final volume of 20 μl, and PCR was performed. In this connection, denaturation(95° C., 30 seconds), annealing (60° C., 30 seconds) and extension (72° C., 45 seconds) were carried out for 30 cycles, respectively, using a thermocycler (Model 9600, Perkin-Elmer Cetus, USA).

The PCR products thus amplified were electrophoresed on 3% agarose gel. As a result, it was found that the rpoB genes of only mycobacteria can be amplified by using the said primers, since the rpoB DNA fragments of 342 bp were amplified from 44 mycobacterial species and closely related species such as Rhodococcus, Nocardia and Corynebacterium, while no amplifications were observed from Staphylococcus, Streptococcus, Haemophillus, and enteric bacteria which can usually be isolated from the human body.

EXAMPLE 3

Determination of Nucleotide Sequences of rpoB Gene Fragments

The PCR products(DNAs) amplified in Example 2 were separated by 3% agarose gel electrophoresis, and purified using Qiaex II Gel Extraction Kit (QUIAGEN, Hilden, Germany). Nucleotide sequences (306 bp) of the purified rpoB DNAs except for the two primer sequences were determined by employing an automatic sequencer (ABI, USA). Also, rpoB DNA fragments of 3 kinds of controls shown in Example 1 were also amplified, and their nucleotide sequences were determined in the same manner.

For the sequencing reaction, 60 ng of template DNA, 3.2 pmole of each genus-specific primer and distilled water were mixed in a final volume of 10.5 μl. Then, 4 μl of 5×TACS buffer, 1 μl of dNTP mixture, 4 μl of termination-mixture, and 0.5 μl (5U/μl) of Taq polymerase were added, and the reaction was carried out using 5% (v/v) dimethylsulfoxide for 30 cycles of 15 seconds at 95° C., 10 seconds at 50° C., and 4 minutes at 60° C. Both strands were sequenced for cross-check. FIGS. 1A–G show the nucleotide sequences (306 bp) of the amplified rpoB fragments of the 44 mycobacterial strains and the 3 non-mycobacterial strains. The (G+C) ratio of these amplified DNAs were 63–69%, which reflects the general phenotype of genus Mycobacterium (62–70%).

The nucleotide sequences thus determined were compared with one another for the investigation of pairwise similarity, which revealed that mycobacterial species are closely related with each other and are clearly distinguished from other bacterial genuses. In general, 85–100% similarity was observed among mycobacterial species, and there were no insertion or deletion. Interestingly, members of the M. tuberculosis complex (M. tuberculosis, M. bovis, M. bovis BCG and M. africanum) were identical, which may be an evidence to support a hypothesis that M. bovis is a subspecies of M. tuberculosis as M. avium and M. paratuberculosis are (99.3<percent similarity).

Amino acid sequences deduced from the amplified rpoB DNA demonstrated 101 amino acid residues. As expected, amino acid sequences among mycobacterial species were also highly conserved, while variations were observed at 6 amino acids ($458^{th}$, $468^{th}$, $531^{st}$, $539^{th}$, $541^{st}$ and $552^{nd}$). Interestingly, instead of the $M_{468}$(ATG), which was found uniformly in most of the slow-growing mycobacteria, rapid-growing mycobacteria and M. terrae complex had $L_{468}$ (CTG, TTG or CTC) as non-mycobacteria. Among the investigated mycobacteria, only M. celatum which has been known to be rifampin-resistant had $N_{531}$ (AAC). That is one of the most frequent site of mutation representing rifampin susceptibility in M. tuberculosis[S531→L531 (TCG-TTG)].

EXAMPLE 4

Construction of a Phyogenetic Tree of Mycobacteria

Figure 2B:
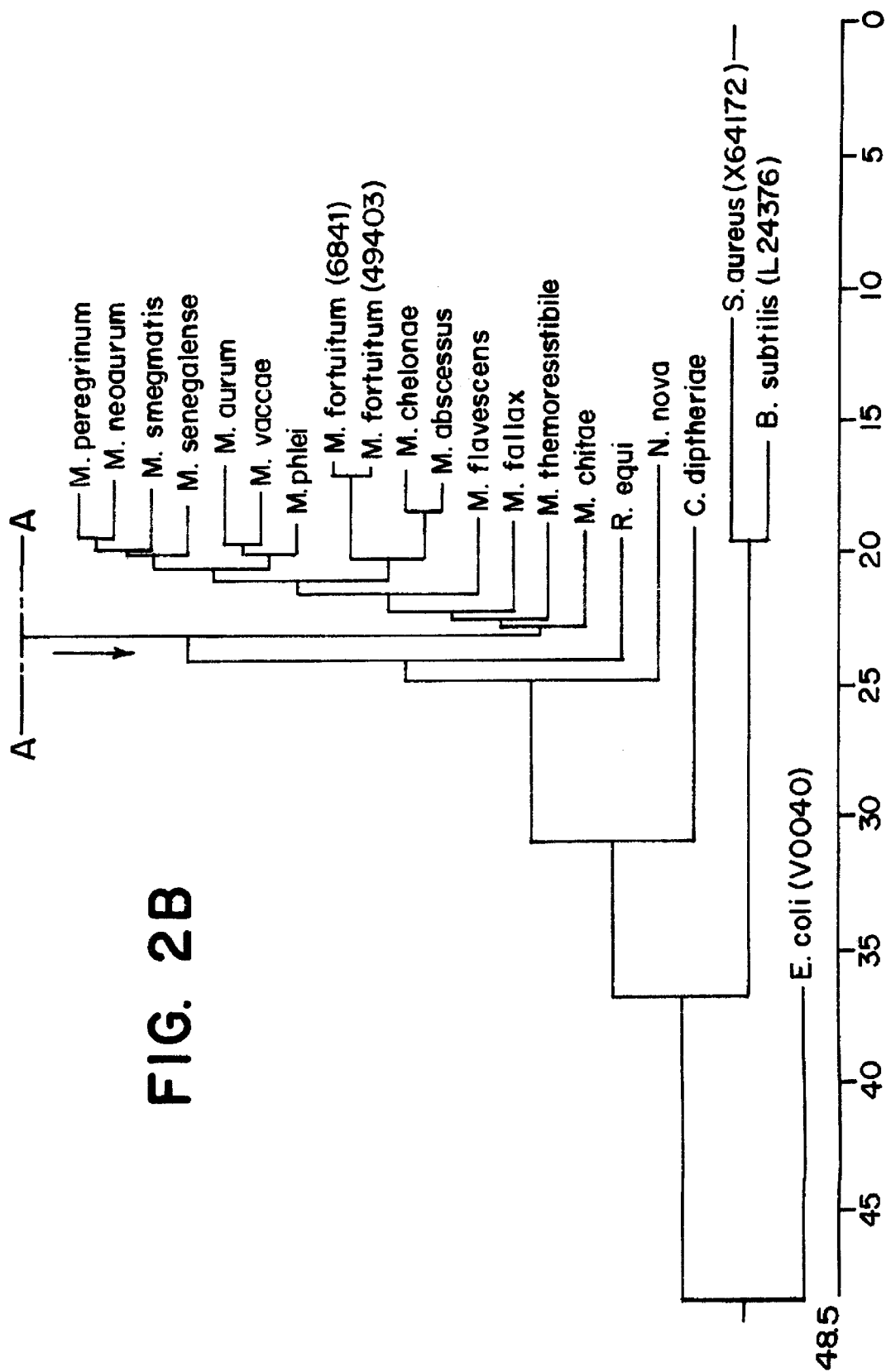

A phylogenetic tree was constructed employing MegAlign package (Windows Version 3.12e, DNASTAR, Madison, Wis., USA) based on the following nucleotide sequences, in accordance with neighborhood joining method (see: FIGS. 2A–B):

1) rpoB DNA fragments (306 bp) of 44 kinds of mycobacteria;

2) the nucleotide sequences of rpoB of Gram-negative E. coli (V00340; ECOLI*), Gram-positive B. subtilis (L24376; BSUBT*), and Gram-positive S. aureus (X64172; SAURE*) registered in Gene Bank; and, 3) the nucleotide sequences of rpoB of C. diphtheriae, N. nova and R. equi.

As can be seen in FIGS. 2A–B, all of tested species showed good identification. An interesting feature is the natural coherence of the classical taxonomic distinction between rapid- and slow-growing species. Rapid-growing species are united to exclude the slow-growing lines. In this phylogenetic tree clustering of pathogenic and potentially pathogenic species is another characteristic. *M. fortuitum, M. chelonae,* and *M. abscessus,* which are included in the taxonomic groups of pathogenic, rapidly growing mycobacteria, form a distinct cluster. *M. haemophilum* is the species closest to *M. leprae* as the result from 23S rRNA sequence analysis (see: Stone, B. B., R. M. Nietupski, G. L. Breton and W. G. Weisberg, Comparison of Mycobacterium 23S rRNA Sequences by High-temperature Reverse Transcription and PCR, Int. J. Syst. Bacteriol., 45:811–819, 1995).

In addition, characteristic findings were observed among the debated and newly recognized species. For example, *M. kansasli* and *M. gastri* are clearly identified in terms of taxonomy, though they were indistinguishable from each other by a conventional 16S rRNA sequence analysis. *M. intracellulare,* which has been long regarded to be closely related to *M. avium,* is close to *M. asiaticum,* whereas *M. avium* is clustered with *M. paratuberculosis, M. celatum* and *M. scrofulaceum.* On the other hand, *M. celatum* is distinctly separated from *M. avium, M. paratuberculosis* and *M. scrofulaceum,* which suggests that it can reasonably be regarded as a distinct species.

EXAMPLE 5

Figure 3A:
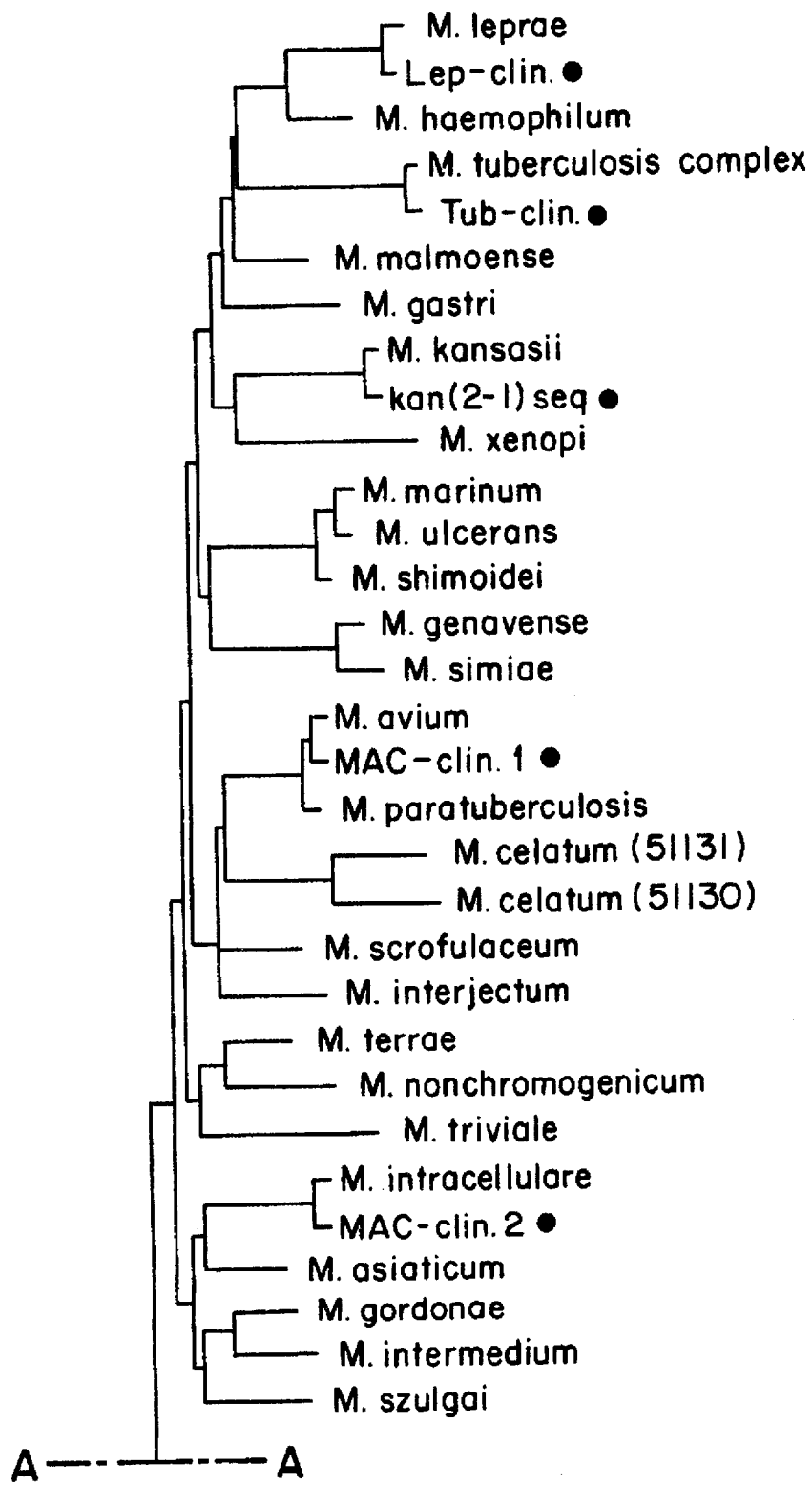
FIGS. 3A–B show results of identification of clinical isolates by determining the phylogenetic relationship.
Figure 3B:
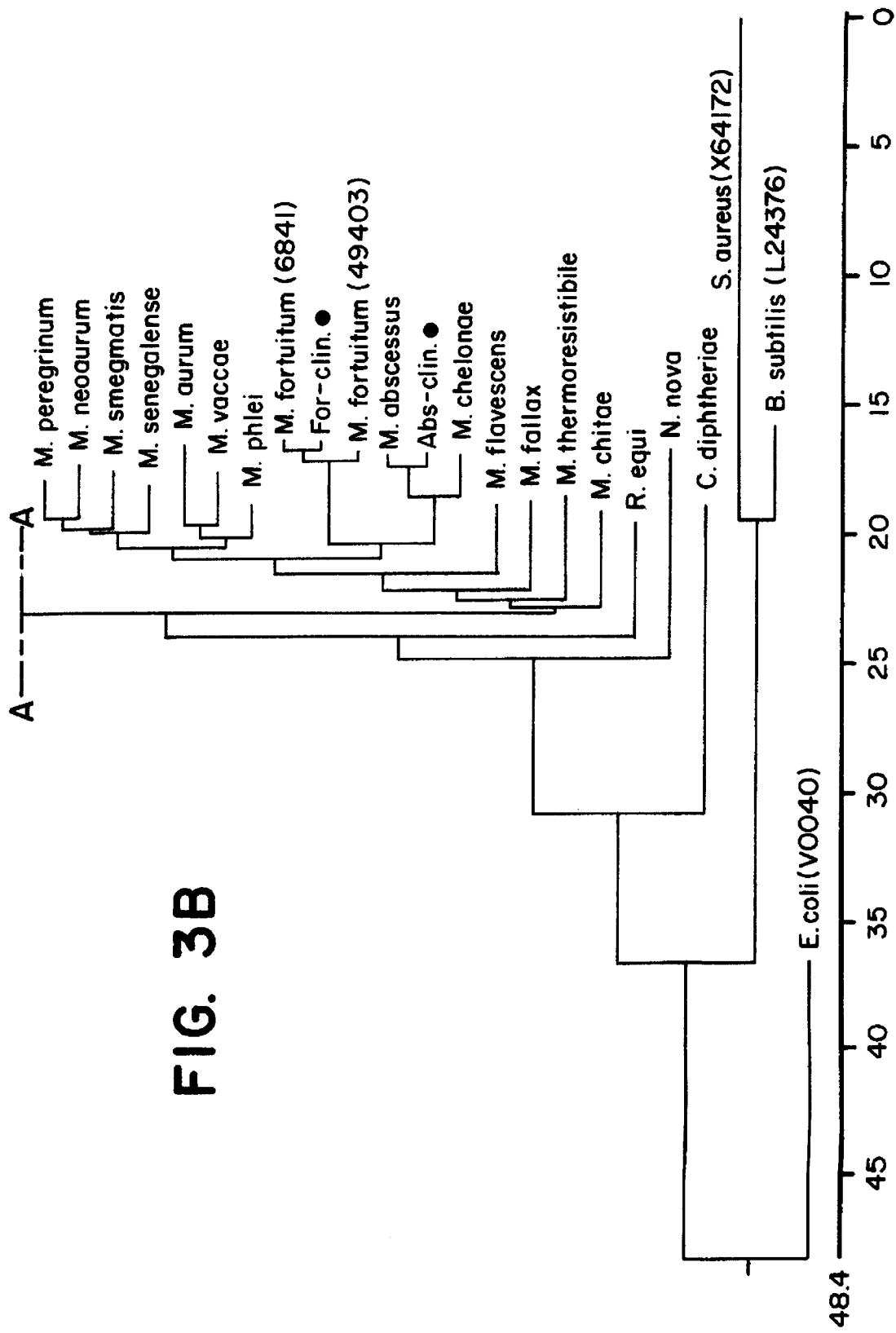

Identification of Clinically Isolated Mycobacterial Species (wild type) from Patients In order to investigate whether comparative rpoB DNA sequencing can be really applied to wild type mycobacteria, i.e., clinically isolated species from patients, 7 mycobacterial species which were isolated from patients and had already been identified biochemically, were employed. Amplification and PCR-mediated sequencing of rpoB gene fragments were accomplished according to the methods disclosed in Examples 2 and 3, respectively. And then, phylogenetic relationship was determined by inferring a phylogenetic tree together with the reference species disclosed in Table 1 (see: FIGS. 3A–B). In FIGS. 3A–B, Lep-clin.●, Tub-clin.●, Kan(2-1).seq●, MAC-clin.1●, MAC-clin.2●, For-clin. ● and Abs-clin.● represent the 7 clinical isolates of microbacteria, respectively. As a result, *M. leprae, M. tuberculosis,* MAC, *M. kansasii, M. fortuitum,* and *M. abscessus* which had been confirmed in the conventional way, were successfully identified by forming a tight cluster with known reference species. Only two nucleotides were changed in the clinical isolate of *M. leprae* [$T_{491}$ (AC G→AC$\underline{C}$), $L_{538}$ ($\underline{T}$TG→$\underline{C}$TG)]. Others showed one nucleotide difference or identical rpoB sequences with the type strains. Further, the clinical isolate of *M. tuberculosis,* i.e., Tub-clin.● was found to have a missense mutation of $S_{531}$→$L_{531}$(T$\underline{C}$G→T$\underline{T}$G) and rifampin resitance.

These above results illustrate that: rpoB sequences from 44 mycobacterial species provide a basis for systematic phylogenetic relationship that can be used to identify clinically isolated mycobacteria that are pathogenic or potentially so; and, therefore, PCR-mediated sequence analysis of rpoB DNA can be regarded as a reliable and rapid method for the diagnosis of mycobacterial infection.

As clearly illustrated and demonstrated as aboves, the present invention provides a method for diagnosis of mycobacterial infection by comparative sequence analysis of rpoB gene coding for β-subunit of RNA polymerase. In accordance with the present invention, it was found that: rpoB sequences from 44 mycobacterial species provide a basis for systematic phylogenetic relationship which can be used to identify clinically isolated mycobacteria that are pathogenic or potentially so. Accordingly, the amplification of rpoB DNA followed by automated sequencing and the analysis of phylogenetic relationships with the reference species can be used efficiently to detect and identify clinical isolates of mycobacteria which have not been identified by the conventional methods. In particular, this approach is useful for slowly growing, fastidious or uncultivable mycobacteria. Furthermore, in the case of *M. tuberculosis,* rifampin susceptibility can be simultaneously determined. Thus, the PCR-mediated comparative sequence analysis of rpoB DNA of the invention can be regarded as a reliable and rapid method for the diagnosis of mycobacterial infection.

What is claimed is:

1. A pair of isolated PCR primers for sequence-specific amplification of rpoB gene of mycobacterial species whose nucleotide sequences consist of SEQ ID NO: 48 and SEQ ID NO:49.

2. An rpoB gene fragment amplified by using isolated genomic DNA of *Mycobacterium abscessus* as a template and both of the PCR primers of claim 1, the nucleotide sequence of said fragment consisting of SEQ ID NO:1.

3. An rpoB gene fragment amplified by using isolated genomic DNA of *Mycobacteriurn africanum* as a template and both of the PCR primers of claim 1, the nucleotide sequence of said fragment consisting of SEQ ID NO:2.

4. An rpoB gene fragment amplified by using isolated genomic DNA of *Mycobacterium asiatictim* as a template and both of the PCR primers of claim 1, the nucleotide sequence of said fragment consisting of SEQ ID NO:3.

5. An rpoB gene fragment amplified by using isolated genomic DNA of *Mycobacterium aurum* as a template and both of the PCR primers of claim 1, the nucleotide sequence of said fragment consisting of SEQ ID NO:4.

6. An rpoB gene fragment amplified by using isolated genomic DNA of *Mycobacterium avium* as a template and both of the PCR primers of claim 1, the nucleotide sequence of said fragment consisting of SEQ ID NO:5.

7. An rpoB gene fragment amplified by using isolated genomic DNA of *Mycobacterium bovis* as a template and both of the PCR primers of claim 1, the nucleotide sequence of said fragment consisting of SEQ ID NO:6.

8. An rpoB gene fragment amplified by using isolated genomic DNA of *Mycobacterium bovis* BCG as a template and both of the PCR primers of claim 1, the nucleotide sequence of said fragment consisting of SEQ ID NO:7.

9. An rpoB gene fragment amplified by using isolated genomic DNA of *Mycobacterium celatum* type I as a template and both of the PCR primers of claim 1, the nucleotide sequence of said fragment consisting of SEQ ID NO:8.

10. An rpoB gene fragment amplified by using isolated genomic DNA of *Mycobacterium celatunm* type II as a template and both of the PCR primers of claim 1, the nucleotide sequence of said fragment consisting of SEQ ID NO:9.

11. An rpoB gene fragment amplified by using isolated genomic DNA of *Mycobacterium chelonae* as a template and both of the PCR primers of claim 1, the nucleotide sequence of said fragment consisting of SEQ ID NO:10.

12. An rpoB gene fragment amplified by using isolated genomic DNA of *Mycobacterium chitae* as a template and both of the PCR primers of claim 1, the nucleotide sequence of said fragment consisting of SEQ ID NO:11.

13. An rpoB gene fragment amplified by using isolated genomic DNA of *Mycobacterium fallax* as a template and both of the PCR primers of claim 1, the nucleotide sequence of said fragment consisting of SEQ ID NO:12.

14. An rpoB gene fragment amplified by using isolated genomic DNA of *Mycobacterium flavescense* as a template and both of the PCR primers of claim 1, the nucleotide sequence of said fragment consisting of SEQ ID NO:13.

15. An rpoB gene fragment amplified by using isolated genomic DNA of *Mycobacterium fortuitum* as a template and both of the PCR primers of claim 1, the nucleotide sequence of said fragment consisting of SEQ ID NO:14.

16. An rpoB gene fragment amplified by using isolated genomic DNA of *Mycobacterium fortuitum* 49403 as a template and both of the PCR primers of claim 1, the nucleotide sequence of said fragment consisting of SEQ ID NO:15.

17. An rpoB gene fragment amplified by using isolated genomic DNA of *Mycobacterium gastri* as a template and both of the PCR primers of claim 1, the nucleotide sequence of said fragment consisting of SEQ ID NO:16.

18. An rpoB gene fragment amplified by using isolated genomic DNA of *Mycobacterium genavense* as a template and both of the PCR primers of claim 1, the nucleotide sequence of said fragment consisting of SEQ ID NO:17.

19. An rpoB gene fragment amplified by using isolated genomic DNA of *Mycobacterium gordonae* as a template and both of the PCR primers of claim 1, the nucleotide sequence of said fragment consisting of SEQ ID NO:18.

20. An rpoB gene fragment amplified by using isolated genomic DNA of *Mycobacterium haemophilum* as a template and both of the PCR primers of claim 1, the nucleotide sequence of said fragment consisting of SEQ ID NO:19.

21. An rpoB gene fragment amplified by using isolated genomic DNA of *Mycobacterium interjectum* as a template and both of the PCR primers of claim 1, the nucleotide sequence of said fragment consisting of SEQ ID NO:20.

22. An rpoB gene fragment amplified by using isolated genomic DNA of *Mycobacterium intermedium* as a template and both of the PCR primers of claim 1, the nucleotide sequence of said fragment consisting of SEQ ID NO:21.

23. An rpoB gene fragment amplified by using isolated genomic DNA of *Mycobacterium intracellulare* as a template and both of the PCR primers of claim 1, the nucleotide sequence of said fragment consisting of SEQ ID NO:22.

24. An rpoB gene fragment amplified by using isolated genomic DNA of *Mycobacterium kansasii* as a template and both of the PCR primers of claim 1, the nucleotide sequence of said fragment consistino of SEQ ID NO:23.

25. An rpoB gene fragment amplified by using isolated genomic DNA of *Mycobacterium leprae* (Thai 53) as a template and both of the PCR primers of claim 1, the nucleotide sequence of said fragment consisting of SEQ ID NO:24.

26. An rpoB gene fragment amplified by using isolated genomic DNA of *Mycobacterium malmoense* as a template and both of the PCR primers of claim 1, the nucleotide sequence of said fragment consisting of SEQ ID NO:25.

27. An rpoB gene fragment amplified by using isolated genomic DNA of *Mycobacterium marinum* as a template and both of the PCR primers of claim 1, the nucleotide sequence of said fragment consisting of SEQ ID NO:26.

28. An rpoB gene fragment amplified by using isolated genomic DNA of *Mycobacterium neoaurum* as a template and both of the PCR primers of claim 1, the nucleotide sequence of said fragment consisting of SEQ ID NO:27.

29. An rpoB gene fragment amplified by using isolated genomic DNA of *Mycobacterium nonchromogenicum* as a template and both of the PCR primers of claim 1, the nucleotide sequence of said fragment consisting of SEQ ID NO:28.

30. An rpoB gene fragment amplified by using isolated genomic DNA of *Mycobacterium paratuberculosis* as a template and both of the PCR primers of claim 1, the nucleotide sequence of said fragment consisting of SEQ ID NO:29.

31. An rpoB gene fragment amplified by using isolated genomic DNA of *Mycobacterium peregrinum* as a template and both of the PCR primers of claim 1, the nucleotide sequence of said fragment consisting of SEQ ID NO:30.

32. An rpoB gene fragment amplified by using isolated genomic DNA of *Mycobacterium phlei* as a template and both of the PCR primers of claim 1, the nucleotide sequence of said fragment consisting of SEQ ID NO:31.

33. An rpoB gene fragment amplified by using isolated genomic DNA of *Mycobacterium scrofulaceum* as a template and both of the PCR primers of claim 1, the nucleotide sequence of said fragment consisting of SEQ ID NO:32.

34. An rpoB gene fragment amplified by using isolated genomic DNA of *Mycobacterium senegalense* as a template and both of the PCR primers of claim 1, the nucleotide sequence of said fragment consisting of SEQ ID NO:33.

35. An rpoB gene fragment amplified by using isolated genomic DNA of *Mycobacterium shimoidei* as a template and both of the PCR primers of claim 1, the nucleotide sequence of said fragment consisting of SEQ ID NO:34.

36. An rpoB gene fragment amplified by using isolated genomic DNA of *Mycobacterium simiae* as a template and both of the PCR primers of claim 1, the nucleotide sequence of said fragment consisting of SEQ ID NO:35.

37. An rpoB gene fragment amplified by using isolated genomic DNA of *Mycobacterium smegmatis* as a template and both of the PCR primers of claim 1, the nucleotide sequence of said fragment consisting of SEQ ID NO:36.

38. An rpoB gene fragment amplified by using isolated genomic DNA of *Mycobacterium szulgai* as a template and both of the PCR primers of claim 1, the nucleotide sequence of said fragment consisting of SEQ ID NO:37.

39. An rpoB gene fragment amplified by using isolated genomic DNA of *Mycobacterium terrae* as a template and both of the PCR primers of claim 1, the nucleotide sequence of said fragment consisting of SEQ ID NO:38.

40. An rpoB gene fragment amplified by using isolated genomic DNA of *Mycobacterium thermoresistable* as a template and both of the PCR primers of claim 1, the nucleotide sequence of said fragment consisting of SEQ ID NO:39.

41. An rpoB gene fragment amplified by using isolated genomic DNA of *Mycobacterium triviale* as a template and both of the PCR primers of claim 1, the nucleotide sequence of said fragment consisting of SEQ ID NO:40.

42. An rpoB gene fragment amplified by using isolated genomic DNA of *Mycobacteriuim ulcerans* as a template and both of the PCR primers of claim 1, the nucleotide sequence of said fragment consisting of SEQ ID NO:42.

43. An rpoB gene fragment amplified by using isolated genomic DNA of *Mycobacterium vaccae* as a template and both of the PCR primers of claim 1, the nucleotide sequence of said fragment consisting of SEQ ID NO:43.

44. An rpoB gene fragment amplified by using isolated genomic DNA of *Mycobacterium xenopi* as a template and both of the PCR primers of claim 1, the nucleotide sequence of said fragment consisting of SEQ ID NO:44.

45. An rpoB gene fragment amplified by using isolated genomic DNA of *Corynebacterium diphtheriae* as a template and both of the PCR primers of claim 1, the nucleotide sequence of said fragment consisting of SEQ ID NO:45.

46. An rpoB gene fragment amplified by using isolated genomic DNA of *Nocardia nova* as a template and both of the PCR primers of claim 1, the nucleotide sequence of said fragment consisting of SEQ ID NO:46.

47. An rpoB gene fragment amplified by using isolated genomic DNA of *Rhodococcus equi* as a template and both of the PCR primers of claim 1, the nucleotide sequence of said fragment consisting of SEQ ID NO:47.

48. A method for detecting and identifying mycobacterial species, comprising the steps of:
 a) amplifying a 342 bp-long fragment of rpoB gene using both of the PCR primers of claim 1 and a template DNA purified from a clinically isolated mycobacterium;
 b) determining a complete DNA sequence of the amplified 342 bp rpoB gene fragment, with the exception of 18nt-long 5' and 3' sequences corresponding to both of said PCR primers, and
 c) inferring a phylogenetic relationship of said DNA sequence to the phylogenetic tree of FIG. 2, said tree having been prepared from the reference sequences shown in FIG. 1 with tlhe use of sequence analysis software.

49. An rpoB gene fragment amplified by using both of the PCR primers of claim 1 and by using as a template genomic DNA isolated from a clinical strain of *Mycobacterium tuberculosis* having a missense mutation of TCG→TTG ($S_{531}$→$L_{531}$), the nucleotide sequence of said fragment consisting of SEQ ID NO:50.

* * * * *

SEQUENCE LISTING

<160> NUMBER OF SEQ ID NOS:    50

<210> SEQ ID NO 1
<211> LENGTH: 306
<212> TYPE: DNA
<213> ORGANISM: Mycobacterium abscessus

<400> SEQUENCE: 1

| | | | | | |
|---|---|---|---|---|---|
| tgcgtaccgt | cggcgagctg | attcagaacc | agatccgggt | cggcctgtcc | cgtatggagc    60 |
| gcgtcgtgcg | tgagcgcatg | accacgcagg | acgtcgaggc | gatcaccccg | cagaccctga   120 |
| tcaacatccg | tcccgtcgtg | gcggcgatca | aggagttctt | cggaaccagc | cagctgtcgc   180 |
| agttcatgga | ccagaacaac | ccgctgtcgg | gcctgaccca | caagcgtcgt | ctgtcggcgc   240 |
| tgggcccgg | tggtctgacc | cgtgaccgcg | ccggcctcga | ggtccgcgac | gtgcacccct   300 |
| cgcact |  |  |  |  |   306 |

<210> SEQ ID NO 2

```
<211> LENGTH: 306
<212> TYPE: DNA
<213> ORGANISM: Mycobacterium africanum

<400> SEQUENCE: 2
tgcgtacggt cggcgagctg atccaaaacc agatccgggt cggcatgtcg cggatggagc      60
gggtggtccg ggagcggatg accacccagg acgtggaggc gatcacaccg cagacgttga     120
tcaacatccg gccggtggtc gccgcgatca aggagttctt cggcaccagc cagctgagcc     180
aattcatgga ccagaacaac ccgctgtcgg ggttgaccca caagcgccga ctgtcggcgc     240
tggggcccgg cggtctgtca cgtgagcgtg ccgggctgga ggtccgcgac gtgcacccgt     300
cgcact                                                                306

<210> SEQ ID NO 3
<211> LENGTH: 306
<212> TYPE: DNA
<213> ORGANISM: Mycobacterium asiaticum

<400> SEQUENCE: 3
tgcgcaccgt gggcgagttg atccagaacc agatccgggt cggcatgtcc cggatggagc      60
gcgtcgtccg cgagcggatg accactcagg acgtcgaggc gatcacgccg cagaccctga     120
tcaacatccg gccggtcgtt gccgcgatca aggagttctt cggcaccagc cagctctcgc     180
agttcatgga ccagaacaac ccgctttcgg gtctgaccca caagcgccgc ctgtcggcgc     240
tgggccccgg cggtctgtcc cgtgagcgtg ccgggctgga agtgcgtgac gtgcacccct     300
cgcact                                                                306

<210> SEQ ID NO 4
<211> LENGTH: 306
<212> TYPE: DNA
<213> ORGANISM: Mycobacterium aurum

<400> SEQUENCE: 4
tgcgtaccgt cggcgagctg atccagaacc agatccgcgt cggcctctcg cgtatggagc      60
gtgtcgtgcg tgagcgcatg accacccagg acgtcgaggc gatcacgccg cagaccctga     120
tcaacatccg tcccgtcgtg gcggcgatca aggagttctt cggcacgtcg cagctgtcgc     180
agttcatgga ccagaacaac ccgctgtcgg gtctgaccca caagcgccgc ctgtcggcgc     240
tgggcccggg tggtctgtcc cgtgagcgcg ccggcctcga ggtccgcgac gtgcactcca     300
gccact                                                                306

<210> SEQ ID NO 5
<211> LENGTH: 306
<212> TYPE: DNA
<213> ORGANISM: Mycobacterium avium

<400> SEQUENCE: 5
tgcgcaccgt cggtgagctg atccagaacc agatccgggt cggcatgtcc cggatggagc      60
gcgtcgtccg cgagcggatg accacccagg acgtcgaggc catcacgccg cagaccctga     120
tcaacatccg tcccgtcgtg gcggcgatca aggagttctt cggcaccagc cagctgtccc     180
agttcatgga ccagaacaac ccgctgtcgg ggctcaccca caagcgccgc ctgtcggcgc     240
tgggcccggg tggtctgtcc cgggagcggg ccgggctgga ggtccgcgac gtgcacccgt     300
cccact                                                                306
```

-continued

<210> SEQ ID NO 6
<211> LENGTH: 306
<212> TYPE: DNA
<213> ORGANISM: Mycobacterium bovis

<400> SEQUENCE: 6
tgcgtacggt cggcgagctg atccaaaacc agatccgggt cggcatgtcg cggatggagc 60
gggtggtccg ggagcggatg accacccagg acgtggaggc gatcacaccg cagacgttga 120
tcaacatccg gccggtggtc gccgcgatca aggagttctt cggcaccagc cagctgagcc 180
aattcatgga ccagaacaac ccgctgtcgg ggttgaccca caagcgccga ctgtcggcgc 240
tggggcccgg cggtctgtca ccgtgacgtg ccgggctgga ggtccgcgac gtgcacccgt 300
cgcact 306

<210> SEQ ID NO 7
<211> LENGTH: 306
<212> TYPE: DNA
<213> ORGANISM: Mycobacterium bovis BCG

<400> SEQUENCE: 7
tgcgtacggt cggcgagctg atccaaaacc agatccgggt cggcatgtcg cggatggagc 60
gggtggtccg ggagcggatg accacccagg acgtggaggc gatcacaccg cagacgttga 120
tcaacatccg gccggtggtc gccgcgatca aggagttctt cggcaccagc cagctgagcc 180
aattcatgga ccagaacaac ccgctgtcgg ggttgaccca caagcgccga ctgtcggcgc 240
tggggcccgg cggtctgtca cgtgagcgtg ccgggctgga ggtccgcgac gtgcacccgt 300
cgcact 306

<210> SEQ ID NO 8
<211> LENGTH: 306
<212> TYPE: DNA
<213> ORGANISM: Mycobacterium celatum Type1

<400> SEQUENCE: 8
ttcgtaccgt cggtgagctg atccagaacc agatccgagt cggcatgtcc cgcatggagc 60
gggtggtccg cgagcggatg accactcagg acgtcgaggc gatcacgccg cagaccctga 120
tcaacatccg tcccgtcgtg gcggcgatca aggagttctt cggcaccagc cagctctcgc 180
agttcatgga ccagaacaac ccgctgtccg ggctgaccca caagcggcgc ctgaacgcac 240
tgggcccggg tggtctgtcc cgggagcggg cgggcctcga ggtgcgcgac gtgcacccga 300
gtcact 306

<210> SEQ ID NO 9
<211> LENGTH: 306
<212> TYPE: DNA
<213> ORGANISM: Mycobacterium celatum Type2

<400> SEQUENCE: 9
ttcgtaccgt cggcgagctg atccagaacc agatccgggt cggtatgtcg aggatggagc 60
gggtggtccg cgagcggatg accacccagg acgtcgaggc gatcacgccg cagaccctga 120
tcaacatccg tccggtcgtg gcggccatca aggagttctt cggcaccagc cagctctcgc 180
agttcatgga ccagaacaac ccattgtccg ggctgaccca caagcgtcgc ctgaacgcgc 240
tcggcccggg tggtctgtcc cgggagcggg ccggcctgga ggtccgcgac gtgcacccga 300
gccact 306

<210> SEQ ID NO 10
<211> LENGTH: 306
<212> TYPE: DNA
<213> ORGANISM: Mycobacterium chelonae

<400> SEQUENCE: 10

| | |
|---|---|
| tgcgtaccgt cggcgagctg atccagaacc agatccgggt cggcctgtcg cgtatggagc | 60 |
| gcgtcgtgcg tgagcgcatg accactcagg acgtcgaggc gatcaccccg cagaccctga | 120 |
| tcaacatccg tcccgtcgtg gcggcgatca aggagttctt cggaaccagc cagctgtcgc | 180 |
| agttcatgga ccagaacaac ccgctttcgg gtctgaccca caagcgtcgt ctgtcggctc | 240 |
| tgggcccgg tggtctgacc cgtgaccgcg ctggccttga ggtccgcgac gtgcacccct | 300 |
| cgcact | 306 |

<210> SEQ ID NO 11
<211> LENGTH: 306
<212> TYPE: DNA
<213> ORGANISM: Mycobacterium chitae

<400> SEQUENCE: 11

| | |
|---|---|
| tgcgcaccgt gggtgagctg atccagaacc agatccgggt cggcctgtcc cgcatggagc | 60 |
| gcgtcgtgcg cgagcggatg accacccagg acgtcgaggc catcacgccg cagaccctga | 120 |
| tcaacatccg tcccgtcgtg gcggcgatca aggagttctt cggcaccagc cagctgtcgc | 180 |
| agttcatgga ccagaacaac ccgctgtccg ggctgaccca caagcgtcgt ctctcggcgc | 240 |
| tcgggcccgg cggtctgtcc cgtgagcgcg ccggtctcga ggttcgtgac gtgcacccgt | 300 |
| cgcact | 306 |

<210> SEQ ID NO 12
<211> LENGTH: 306
<212> TYPE: DNA
<213> ORGANISM: Mycobacterium fallax

<400> SEQUENCE: 12

| | |
|---|---|
| tgcgcaccgt gggcgagctg atccagaacc agatccgggt cggcctgtcc cggatggagc | 60 |
| gcgtcgtccg cgagcggatg accacccagg acgtcgaggc gatcaccccg cagaccctga | 120 |
| tcaacatccg tcccgtggtg gcggcgatca aggagttctt cgggaccagc cagctgtcgc | 180 |
| agttcatgga ccagaacaac ccgctgtcgg gcctgaccca caagcgccgg ctgtccgcgc | 240 |
| ttggccccgg cggtctgtcc cgtgagcgcg ccggcctgga ggtccgcgac gtgcacgcca | 300 |
| gccact | 306 |

<210> SEQ ID NO 13
<211> LENGTH: 306
<212> TYPE: DNA
<213> ORGANISM: Mycobacterium flavescens

<400> SEQUENCE: 13

| | |
|---|---|
| tgcgcaccgt cggcgagctg atccagaacc agatccgggt cggcctgtcg cggatggagc | 60 |
| gcgtcgtccg tgagcggatg accacccagg acgtcgaggc gatcacgccg cagaccctga | 120 |
| tcaacatccg tcccgtcgtg gcggcgatca aggagttctt cggtacgtcg cagctgtcgc | 180 |
| agttcatgga ccagaacaac ccgctgtcgg gtctgaccca caagcgccgc ctgtcggcgc | 240 |
| tgggccccgg tggtctgtcc cgtgagcgcg ccggcctcga agtccgtgac gtgcacccgt | 300 |
| cgcact | 306 |

<210> SEQ ID NO 14
<211> LENGTH: 306
<212> TYPE: DNA
<213> ORGANISM: Mycobacterium fortuitum

<400> SEQUENCE: 14

```
tgcgcaccgt gggcgagctg atccagaacc agatccgcgt cggcctgtcc cgcatggagc      60
gcgtcgtgcg tgagcgcatg accacccagg acgtcgaggc gatcaccccg cagaccctga     120
tcaacatccg tcccgtcgtg gcggcgatca aggagttctt cggaacgtcg cagctgtcgc     180
agttcatgga tcagaacaac ccgctgtcgg gtctgaccca caagcgtcgt ctgtcggcgc     240
tgggccccgg cggtctgtcc cgtgagcgcg ccggccttga ggtccgcgac gtccactcgt     300
cgcact                                                                306
```

<210> SEQ ID NO 15
<211> LENGTH: 306
<212> TYPE: DNA
<213> ORGANISM: Mycobacterium fortuitum 49403

<400> SEQUENCE: 15

```
tgcgcaccgt gggcgagctg atccagaacc agatccgggt cggcctgtcc cgcatggagc      60
gcgtcgtgcg tgagcgcatg accacccagg acgtcgaggc gatcaccccg cagaccctga     120
tcaacatccg tcccgtcgtg gcggcgatca aggagttctt cggaacgtcg cagctgtcgc     180
agttcatgga tcagaacaac ccgctgtcgg gtctgaccca caagcgtcgt ctgtcggcgc     240
tgggccccgg cggtctgtcc cgtgagcgcg ccggccttga ggtccgcgac gtccactcgt     300
cgcact                                                                306
```

<210> SEQ ID NO 16
<211> LENGTH: 306
<212> TYPE: DNA
<213> ORGANISM: Mycobacterium gastri

<400> SEQUENCE: 16

```
tgcgcacggt gggcgagctg atccagaacc agatccgggt cggcatgtcc aggatggagc      60
gcgtcgtccg ggagcggatg accactcagg acgtcgaggc catcacgccg cagacgctga     120
tcaacattcg cccggtggtc gctgccatta aggagttctt cggcaccagc cagctgtcgc     180
agttcatgga ccagaacaac ccgctgtcgg gcctgaccca caagcgccgg ctttcggcgc     240
tgggccccgg cggtctgtca cgtgagcgtg ccgggctgga ggtccgcgac gtgcacccgt     300
cgcact                                                                306
```

<210> SEQ ID NO 17
<211> LENGTH: 306
<212> TYPE: DNA
<213> ORGANISM: Mycobacterium genavense

<400> SEQUENCE: 17

```
tgcgcacggt gggcgatctg atccagaacc agatccgggt cggcatgtcg cggatggagc      60
gggtggtccg tgagcggatg accactcagg acgtcgaggc catcacgccg cagaccctga     120
tcaacatccg tccggttgtg gcggcgatca aggagttctt cggcaccagc cagctctcgc     180
agttcatgga ccagaacaac ccgctgtcag gtctcaccca caagcgccgg ttgtcggcgc     240
tggggccggg cggtctgtcc cgtgagcggg cgggcctcga ggtccgcgac gtgcacccgt     300
```

```
ctcact                                                                  306

<210> SEQ ID NO 18
<211> LENGTH: 306
<212> TYPE: DNA
<213> ORGANISM: Mycobacterium gordonae

<400> SEQUENCE: 18
tgcgcaccgt gggcgagctg atccagaacc agatccgggt cggcatgtcc cggatggagc       60
gcgtcgtgcg cgaccggatg accactcagg acgtcgaggc catcacgccg cagaccctga      120
tcaacatccg gccggtcgtc gccgcgatca aggagttctt cggcaccagc cagctctcgc      180
agttcatgga ccagaacaac ccgctgtcgg gtctgaccca caagcgtcgt ctgtcggcgc      240
tggggccggg tggtctgtcc cgtgagcgtg cgggtctgga agtacgtgac gtgcacccgt      300
cgcact                                                                 306

<210> SEQ ID NO 19
<211> LENGTH: 306
<212> TYPE: DNA
<213> ORGANISM: Mycobacterium haemophilum

<400> SEQUENCE: 19
tgcgcacggt cggcgaattg atccagaacc agatccgggt cggcatgtcg cggatggagc       60
gggtggtccg ggagcggatg accactcagg acgtcgaggc gatcacgccg cagacgctga      120
tcaatatccg gccggtggtg gccgcgatca aggagttctt cggcaccagc cagctgtcgc      180
agttcatgga ccagaacaac ccgctgtccg gcctaaccca caagcgccgg ctgtcggcgc      240
tggggccggg cggtctgtcg cgtgagcgtg ccgggctaga ggtccgcgac gtgcacccgt      300
cgcact                                                                 306

<210> SEQ ID NO 20
<211> LENGTH: 306
<212> TYPE: DNA
<213> ORGANISM: Mycobacterium interjectum

<400> SEQUENCE: 20
tgcgtaccgt cggcgagctg atccagaacc agatccgggt cggcatgtcc cgcatggagc       60
gcgttgtccg cgagcggatg accactcagg acgtcgaggc catcacgccg cagaccttga      120
tcaacatccg gccggtggtc gccgcgatca aggagttctt cggcaccagc cagctctcgc      180
agttcatgga ccagaacaac ccgctgtcgg gtctgaccca caagcgtcgt ctgtcggcgt      240
tgggcccggg tggtctgtcg cgtgagcgtg ccgggctgga agtccgtgac gtgcacccgt      300
cgcact                                                                 306

<210> SEQ ID NO 21
<211> LENGTH: 306
<212> TYPE: DNA
<213> ORGANISM: Mycobacterium intermedium

<400> SEQUENCE: 21
tgcgcaccgt cggtgagctg atccagaacc agatccgggt cggcatgtcc aggatggagc       60
gcgtcgtccg ggagcggatg accacccagg acgtcgaggc gatcacgccg cagacgctga      120
tcaacatccg gccggtcgtc gccgcgatca aggagttctt cggcaccagc cagctgtcgc      180
agttcatgga ccagaacaac ccgctgtcgg gcctcaccca caagcgccgc ctgtcggcgc      240
tgggcccggg cggtctgtcc cgcgagcggg ccggcctcga ggtccgcgac gtgcacccga      300
```

```
accact                                                              306

<210> SEQ ID NO 22
<211> LENGTH: 306
<212> TYPE: DNA
<213> ORGANISM: Mycobacterium intracellulare

<400> SEQUENCE: 22
tgcgcaccgt gggtgagctg atccagaacc agatccgggt cggcatgtcg cggatggagc    60
gcgtcgtccg cgagcggatg accacgcagg acgtcgaggc catcacgccg cagaccctga   120
tcaacatccg gccggtcgtc gccgcgatca aggagttctt cggcaccagc cagctgagcc   180
agttcatgga ccagaacaac ccgctgtccg gtctgaccca caagcgccgc ctctcggcgc   240
tgggccccgg cggtctgtcc cgtgagcgcg ccggcctgga ggtccgtgac gtccaccccct   300 cgcact                                                              306

<210> SEQ ID NO 23
<211> LENGTH: 306
<212> TYPE: DNA
<213> ORGANISM: Mycobacterium kansasii

<400> SEQUENCE: 23
tgcgtaccgt cggcgagctg atccagaacc agatccgggt cggcatgtcg aggatggagc    60
gggtggtccg ggaacggatg accactcagg acgtcgaggc gatcacgccg cagacactga   120
tcaacatccg cccggtggtc gccgccatca aggagttctt cggcaccagc cagctctccc   180
agttcatgga ccagaacaac ccgctgtcgg gcctcaccca caagcgccgg ctttcggcgc   240
tggggccggg cggtctgtcc cgggagcgtg ccgggctgga agtgcgtgac gtgcacccgt   300
cgcact                                                              306

<210> SEQ ID NO 24
<211> LENGTH: 306
<212> TYPE: DNA
<213> ORGANISM: Mycobacterium leprae

<400> SEQUENCE: 24
tgcgcacggt cggcgaattg atccagaacc agatccgggt cggtatgtcg cggatggagc    60
gggtggtccg ggagcggatg accacgatca cgccgcagac gctgatcaat atccgtccgg   120
tggtcgccgc tatcaaggaa ttcttcggca ccagccagct gtcgcagttc atggatcaga   180
acaaccctct gtcgggcctg acccacaagc gccggctgtc ggcgctgggc ccgggtggtt   240
tgtcgcgtga gcgtgccggg ctagaggtcc gtgacgtgca cccttcgcac tccaggacgt   300
cgaggc                                                              306

<210> SEQ ID NO 25
<211> LENGTH: 306
<212> TYPE: DNA
<213> ORGANISM: Mycobacterium malmoense

<400> SEQUENCE: 25
tgcgcacggt cggggagctg atccagaacc agatccgcgt cggcatgtcg cggatggagc    60
gcgtcgtccg ggagcggatg accacccagg acgtcgaggc gatcacgccg cagacgctga   120
tcaacatccg gccggtggtc gccgcgatca aggagttctt cggcaccagc cagctgtcgc   180
agttcatgga ccagaacaac ccgctgtcgg ggctgaccca caagcgccgg ctgtcggcgc   240
```

-continued

| tgggcccggg tggtctgtcg cgtgagcgtg ccggcttgga ggtccgtgac gtgcacccgt | 300 |
| cgcact | 306 |

<210> SEQ ID NO 26
<211> LENGTH: 306
<212> TYPE: DNA
<213> ORGANISM: Mycobacterium marinum

<400> SEQUENCE: 26

| tgcgcacggt gggtgagctg atccagaacc agatccgggt cggcatgtcg cggatggagc | 60 |
| gggtggtccg ggagcggatg accacccagg acgtcgaggc gatcacgccg cagacgctga | 120 |
| tcaacatccg tccggtcgtt gcggcgatca aggagttctt cggaaccagc cagctgtcgc | 180 |
| agttcatgga ccagaacaac ccgctctccg gtctcaccca aagcgccgc ctctcggcgc | 240 |
| tggggccggg cggtctgtcc cgtgagcgcg ccggtctgga agttcgtgac gtgcacccgt | 300 |
| cgcact | 306 |

<210> SEQ ID NO 27
<211> LENGTH: 306
<212> TYPE: DNA
<213> ORGANISM: Mycobacterium neoaurum

<400> SEQUENCE: 27

| tgcgcaccgt gggtgagctg atccagaatc agatccgggt cggcctgtcg cgcatggagc | 60 |
| gggtcgtgcg cgagcgcatg accacccagg acgtcgaggc gatcaccccg cagaccctga | 120 |
| tcaacatccg tcccgtcgtg gcggcgatca aggagttctt cgggaccagc cagctgtcgc | 180 |
| agttcatgga ccagaacaac ccgctgtcgg gtctgaccca aagcgtcgt ctgtcggcgc | 240 |
| tgggccccgg tggtctgtcc cgtgagcgtg ccggacttga ggtccgcgac gtgcactcca | 300 |
| gccact | 306 |

<210> SEQ ID NO 28
<211> LENGTH: 306
<212> TYPE: DNA
<213> ORGANISM: Mycobacterium nonchromogenicum

<400> SEQUENCE: 28

| tgcgcaccgt gggtgagctg atccagaacc agatccgggt cgggctgtcc cggatggagc | 60 |
| gcgtggtccg cgagcggatg accacccagg acgtcgaggc catcacgccg cagaccctga | 120 |
| tcaacatccg cccggtggtc gccgccatca aggaattctt cggcaccagc cagctgtcgc | 180 |
| agttcatgga ccagaacaac ccgctgtcag gtctgaccca aagcggcgt ctgtcggcgc | 240 |
| tgggcccgg tggtctgtcg cgtgagcgcg ccggcctgga agttcgtgac gtgcacccgt | 300 |
| cccact | 306 |

<210> SEQ ID NO 29
<211> LENGTH: 306
<212> TYPE: DNA
<213> ORGANISM: Mycobacterium paratuberculosis

<400> SEQUENCE: 29

| tgcgcaccgt cggtgagctg atccagaacc agatccgggt cggcatgtcc cggatggagc | 60 |
| gcgtcgtccg cgagcggatg accacccagg acgtcgaggc catcacgccg cagaccctga | 120 |
| tcaacatccg tccgtcgtg gcggcgatca aggagttctt cggcaccagc cagttgtccc | 180 |
| agttcatgga ccagaacaac ccgctgtcgg ggctcaccca aagcgccgc ctgtcggcgc | 240 |

```
tgggcccggg tggtctgtcc cgggagcgtg ccgggctgga ggtccgcgac gtgcacccgt    300
cccact                                                              306
```

<210> SEQ ID NO 30
<211> LENGTH: 306
<212> TYPE: DNA
<213> ORGANISM: Mycobacterium peregrinum

<400> SEQUENCE: 30

```
tgcgcaccgt cggtgagctg atccagaacc agatccgggt cggcctgtcg cgtatggagc     60
gtgtcgtgcg tgagcgcatg accacccagg acgtcgaggc gatcaccccg cagaccctga    120
tcaacatccg ccccgtcgtg gcggcgatca aggagttctt cggcaccagc cagctgtcgc    180
agttcatgga ccagaacaac ccgctgtcgg gtctgaccca caagcgtcgt ctgtcggcgc    240
tgggccccgg cggtctgtcc cgtgagcgcg ccggccttga ggtccgcgac gtgcactcca    300
gccact                                                              306
```

<210> SEQ ID NO 31
<211> LENGTH: 306
<212> TYPE: DNA
<213> ORGANISM: Mycobacterium phlei

<400> SEQUENCE: 31

```
tgcgcaccgt cggcgagctg atccagaacc agatccgggt cggcctgtcg cgtatggagc     60
gcgtcgtgcg cgagcgcatg accacccagg acgtcgaggc gatcacgccg cagaccctga    120
tcaacatccg tcccgtcgtg gcggcgatca aggagttctt cggcaccagc cagctgtcgc    180
agttcatgga ccagaacaac ccgctgtcgg gtctgaccca caagcgccgc ctgtcggcgc    240
tgggcccggg cggtctgtcc cgtgagcgcg ccggcctcga ggtccgcgac gtgcaccaca    300
gccact                                                              306
```

<210> SEQ ID NO 32
<211> LENGTH: 306
<212> TYPE: DNA
<213> ORGANISM: Mycobacterium scrofulaceum

<400> SEQUENCE: 32

```
tgcgcaccgt cggggagctg atccagaacc agatccgggt cggcatgtcc cgcatggagc     60
gggtcgtccg cgagcggatg accacgcagg acgtcgaggc gatcacgccg cagaccctga    120
tcaacatccg gccggtcgtg gccgcgatca aggagttctt cggcaccagc cagctctcgc    180
agttcatgga ccagaacaac ccgctgtcgg gcctgaccca caagcgccgc ctgtcggcgc    240
tgggcccggg tggtctgtcc cgcgagcggg ccgggctgga ggtccgggac gtgcacccgt    300
cgcact                                                              306
```

<210> SEQ ID NO 33
<211> LENGTH: 306
<212> TYPE: DNA
<213> ORGANISM: Mycobacterium senegalense

<400> SEQUENCE: 33

```
tgcgcaccgt gggtgagctg atccagaacc agatccgggt cggcctgtcc cgcatggagc     60
gcgtcgtgcg tgagcggatg accacccagg acgtcgaggc gatcacgccg cagaccctga    120
tcaacatccg tcccgtcgtg gcggcgatca aggagttctt cggtaccagc cagctgtcgc    180
```

```
agttcatgga ccagaacaac ccgctttcgg gtctgaccca caagcgtcgc ctgtcggcgc    240
tgggccccgg cggtctgtcc cgtgagcgtg ccggccttga ggtccgcgac gtgcacgcca    300
gccact                                                              306
```

<210> SEQ ID NO 34
<211> LENGTH: 306
<212> TYPE: DNA
<213> ORGANISM: Mycobacterium shimoidei

<400> SEQUENCE: 34

```
tgcgcacggt gggtgagctg atccagaacc agatccgggt cggcatgtcg cggatggagc    60
gggtggtccg ggagcggatg accacccagg acgtcgaggc gatcacgccg cagacgctga   120
tcaacatccg tccggtcgtt gccgcgatca aggagttctt cggaaccagc cagctgtcgc   180
agttcatgga ccagaacaac ccgctgtccg gtctcaccca caagcgccgc ctctcggcgc   240
tggggccggg cggtctgtcc cgtgagcgtg ccgggctgga agttcgtgac gtgcacccgt   300
cgcact                                                              306
```

<210> SEQ ID NO 35
<211> LENGTH: 306
<212> TYPE: DNA
<213> ORGANISM: Mycobacterium simiae

<400> SEQUENCE: 35

```
tgcgcacggt gggcgaactg atccaaaacc agatccgcgt cggcatgtcg cgtatggagc    60
gtgtcgtccg tgagcggatg accactcagg acgtcgaggc catcacgccg cagaccctga   120
tcaacatccg tccggttgtg gcggcgatca aggagttctt cggcaccagc cagctctcgc   180
agttcatgga ccagaacaac ccgctgtcag gtctcaccca caagcgccgg ttgtcggcgc   240
tggggccggg cggtctgtcc cgtgagcggg cgggcctcga ggtccgcgac gtgcacccgt   300
cgcact                                                              306
```

<210> SEQ ID NO 36
<211> LENGTH: 306
<212> TYPE: DNA
<213> ORGANISM: Mycobacterium smegmatis

<400> SEQUENCE: 36

```
tgcgcaccgt cggtgagctg atccagaacc agatccgcgt gggcctgtcc cgcatggagc    60
gtgtcgtgcg tgagcgcatg accacccagg acgtcgaggc gatcacgccg cagaccctga   120
tcaacatccg tcccgtcgtg gcggcgatca aggagttctt cggcaccagc cagctgtcgc   180
agttcatgga ccagaacaac ccgctgtcgg gtctgaccca caagcgtcgt ctttcggcgc   240 tgggcccccgg cggtctgtcc cgtgagcgcg ctggcctcga ggtccgcgac gtgcaccccca   300 gccact                                                              306
```

<210> SEQ ID NO 37
<211> LENGTH: 306
<212> TYPE: DNA
<213> ORGANISM: Mycobacterium szulgai

<400> SEQUENCE: 37

```
tgcgcaccgt gggcgagttg attcagaacc agatccgggt cggcatgtcc cggatggagc    60
gcgtcgtgcg cgagcggatg accacccagg acgtcgaggc gatcacgccg cagaccctga   120
tcaacatccg gcccgtcgtc gccgcgatca aggagttctt cggcaccagc cagctctcgc   180
```

```
agttcatgga ccagaacaac ccgctctccg gtctgacgca caagcggcgt ctgtccgctc     240
tggggccggg cggtctgtcc cgtgagcggg ccgggctgga ggtccgtgac gtgcacccgt     300
cgcact                                                                306

<210> SEQ ID NO 38
<211> LENGTH: 306
<212> TYPE: DNA
<213> ORGANISM: Mycobacterium terrae

<400> SEQUENCE: 38
tgcgcacggt gggtgagctg atccagaacc agatccgggt cgggttgtcc cggatggagc      60
gtgtggtccg cgagcggatg accacccagg acgtcgaggc catcacgccg cagaccctga     120
tcaacatccg cccggtggtc gccgcgatca aggagttctt cggcaccagc cagctctcgc     180
agttcatgga ccagaacaac ccgctgtcgg gtctgaccca caagcgccgg ctgtcggcgc     240
tgggcccggg tggtctgtcc cgtgagcgtg ccgggcttga ggtccgtgac gtgcacccgt     300
cccact                                                                306

<210> SEQ ID NO 39
<211> LENGTH: 306
<212> TYPE: DNA
<213> ORGANISM: Mycobacterium thermoresistibile

<400> SEQUENCE: 39
tgcgcaccgt cggcgagctg atccagaacc agatccgggt cggcctgtcc cgcatggagc      60
gcgtcgtgcg cgagcggatg accacccagg acgtcgaggc gatcacgccg cagaccctga     120
tcaacatccg ccccgtcgtg gcggcgatca aggagttctt cggcaccagc cagctgagcc     180
agttcatgga ccagaacaac ccgctgtcgg gtctgaccca caagcgccgg ctgtcggcgc     240
tgggcccggg cggtctgagc cgggagcgcg ccggcctcga ggtccgcgac gtccacccgt     300
cgcact                                                                306

<210> SEQ ID NO 40
<211> LENGTH: 306
<212> TYPE: DNA
<213> ORGANISM: Mycobacterium triviale

<400> SEQUENCE: 40
tgcgcaccgt cggggagttg atccagaacc agatccgggt cgggctgtcc cggatggagc      60
gggtggtgcg cgagcggatg accacccagg atgtcgaggc gatcacgccg cagaccctga     120
tcaacatccg cccggtggtc gccgcgatca aggagttctt cggcaccagc cagctgtcgc     180
agttcatgga ccagaacaac ccgctgtccg ggctgaccca caagcgccgg ctgtcggcgc     240 tggggccgg cgggctctcc cgggagcggg ccgggctgga ggtccgcgac gtgcacccca     300
gccact                                                                306

<210> SEQ ID NO 41
<211> LENGTH: 306
<212> TYPE: DNA
<213> ORGANISM: Mycobacterium tuberculosis

<400> SEQUENCE: 41
tgcgtacggt cggcgagctg atccaaaacc agatccgggt cggcatgtcg cggatggagc      60
gggtggtccg ggagcggatg accacccagg acgtggaggc gatcacaccg cagacgttga     120
```

```
tcaacatccg gccggtggtc gccgcgatca aggagttctt cggcaccagc cagctgagcc    180
aattcatgga ccagaacaac ccgctgtcgg ggttgaccca caagcgccga ctgtcggcgc    240
tggggcccgg cggtctgtca cgtgagcgtg ccgggctgga ggtccgcgac gtgcacccgt    300
cgcact                                                                306
```

```
<210> SEQ ID NO 42
<211> LENGTH: 306
<212> TYPE: DNA
<213> ORGANISM: Mycobacterium ulcerans

<400> SEQUENCE: 42
```

```
tgcgcacggt gggtgagctg atccagaacc agatccgggt cggcatgtcg cggatggagc     60
gggtggtccg ggagcggatg accacccagg atgtcgaggc gatcacgccg cagacgctga    120
tcaacatccg tccggtcgtt gccgcgatca aggagttctt cggaaccagc cagctgtcgc    180
agttcatgga ccagaacaac ccgctctccg gtctcaccca caagcgccgc ctctcggcgc    240
tggggccggg cggtctgtcc cgtgagcgcg ccggtctgga agttcgtgac gtgcacccgt    300
cgcact                                                                306
```

```
<210> SEQ ID NO 43
<211> LENGTH: 306
<212> TYPE: DNA
<213> ORGANISM: Mycobacterium vaccae

<400> SEQUENCE: 43
```

```
tgcgcacggt cggtgagctg atccagaacc agatccgcgt cggcctctcg cgtatggagc     60
gtgtcgtccg cgagcggatg accacccagg acgtcgaggc gatcactccg cagaccctga    120
tcaacatccg tcccgtcgtg gcggcgatca aggaattctt cggcaccagc cagctgtcgc    180
agttcatgga ccagaacaac ccgctgtcgg gtctgaccca caagcgtcgc ctgtcggcgc    240 tgggcccccgg cggtctgtcc cgtgagcgcg ccggcctcga ggtccgcgac gtgcactcca    300
gccact                                                                306
```

```
<210> SEQ ID NO 44
<211> LENGTH: 306
<212> TYPE: DNA
<213> ORGANISM: Mycobacterium xenopi

<400> SEQUENCE: 44
```

```
tgcgcacggt cggcgagctg atccaaaacc agatccgggt cggcatgtcg aggatggagc     60
gggtggtccg cgagcggatg accactcagg acgtcgaggc gatcaccccg cagaccttga    120
tcaacatccg ccccgtggtg gccgcgatca aggagttctt cggcaccagc cagctctcgc    180
agttcatgga tcagaacaac ccgctgtcgg ggctcaccca caagcggcgg ctctcggcgc    240
ttggtccggg cggtctgtcg cgcgagcggg ccgggctgga ggtccgtgac gtgcactcga    300
gccact                                                                306
```

```
<210> SEQ ID NO 45
<211> LENGTH: 306
<212> TYPE: DNA
<213> ORGANISM: Corynebacterium diphtheriae

<400> SEQUENCE: 45
```

```
tgcgtaccgt cggcgagctg atccaaaacc aggttcgtgt gggtctctcc cgcatggagc     60
gcgttgttcg cgagcgcatg accactcagg atgctgagtc gatcacccct acctcgctga    120
```

```
tcaacgttcg ccctgtttct gccgccatcc gcgagttctt cggaacctca cagctatcgc    180
agttcatgga ccagaacaac tctctgtccg gtctgaccca caagcgtcgt ctctccgcac    240
tgggcccagg tggcctgtcg cgtgagcgcg ccggcattga ggtccgagac gttcacgctt    300
ctcact                                                              306
```

```
<210> SEQ ID NO 46
<211> LENGTH: 306
<212> TYPE: DNA
<213> ORGANISM: Nocardia nova

<400> SEQUENCE: 46
tccgcacggt cggcgagttg atccagaacc agatccgcgt cggcctctcg cggatggagc    60
gggtggtccg ggaacggatg accacccagg acgtcgaggc catcactccg cagaccctga   120
tcaacatccg tccgatcacg gcggcgctcc gggagttctt cggcacctca cagctgtcgc   180
agttcatgga ccaaaacaac ccactgtcgg gtctgaccca caagcgtcga ctctcggcgc   240
tggggcccgg tggtctgtcc cgtgagcgcg ccggcctgga agtccgcgac gtgcacccct   300
cgcact                                                              306
```

```
<210> SEQ ID NO 47
<211> LENGTH: 306
<212> TYPE: DNA
<213> ORGANISM: Rhodococcus equi

<400> SEQUENCE: 47
tgcgcacggt gggcgagctg atccagaacc agatccgcgt gggcctgtcc cgcatggagc    60
gcgtcgtccg cgagcgcatg acgactcagg acgtcgaggc gatcacgccg cagaccctga   120
tcaacatccg cccggtcgtc gccgcgatca aggagttctt cggaacctcc cagctgtcgc   180
agttcatgga ccagaacaac ccgctgtcgg gcctgaccca caagcgtcgt ctgtcggcgc   240
tgggccccgg cggtctgtcc cgtgagcgcg ccggcctcga ggtgcgagac gtccacccgt   300
cgcact                                                              306
```

```
<210> SEQ ID NO 48
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 48
cgaccacttc ggcaaccg                                                  18
```

```
<210> SEQ ID NO 49
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 49
tcgatcgggc acatccgg                                                  18
```

```
<210> SEQ ID NO 50
<211> LENGTH: 306
<212> TYPE: DNA
<213> ORGANISM: Mycobacterium tuberculosis
```

-continued

```
<400> SEQUENCE: 50
tgcgtacggt cggcgagctg atccaaaacc agatccgggt cggcatgtcg cggatggagc      60
gggtggtccg ggagcggatg accacccagg acgtggaggc gatcacaccg cagacgttga     120
tcaacatccg gccggtggtc gccgcgatca aggagttctt cggcaccagc cagctgagcc     180
aattcatgga ccagaacaac ccgctgtcgg ggttgaccca caagcgccga ctgttggcgc     240
tggggcccgg cggtctgtca cgtgagcgtg ccgggctgga ggtccgcgac gtgcacccgt     300
cgcact                                                                306
```